(12) United States Patent
Sawada

(10) Patent No.: US 7,388,676 B2
(45) Date of Patent: Jun. 17, 2008

(54) IMAGE PROCESSING APPARATUS AND REFRACTIVE INDEX DISTRIBUTION MEASURING APPARATUS

(75) Inventor: Yasuhiro Sawada, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 355 days.

(21) Appl. No.: 11/335,393

(22) Filed: Jan. 18, 2006

(65) Prior Publication Data
US 2006/0159332 A1   Jul. 20, 2006

(30) Foreign Application Priority Data
Jan. 19, 2005   (JP) ............................. 2005-012174

(51) Int. Cl.
*G01N 21/41* (2006.01)
(52) U.S. Cl. .................................... 356/517
(58) Field of Classification Search ............... 356/128, 356/517
See application file for complete search history.

(56) References Cited

U.S. PATENT DOCUMENTS

2003/0053036 A1* 3/2003 Fujishima et al. ............ 355/53

2006/0244905 A1* 11/2006 Piers et al. .................. 351/161

FOREIGN PATENT DOCUMENTS

JP   3423486   4/2003

* cited by examiner

*Primary Examiner*—Tarifur R Chowdhury
*Assistant Examiner*—Jonathon D Cook
(74) *Attorney, Agent, or Firm*—Morgan & Finnegan LLP

(57) ABSTRACT

An image processing apparatus is disclosed which can produce refractive index distribution data with high accuracy without limiting directions in which transmitted wavefronts are measured. The image processing apparatus has a simulating section which simulates a transmitted wavefront in each of the directions to produce a second transmitted wavefront image based on first refractive index distribution data, a comparing section which produces first information indicating the result of comparison between the second transmitted wavefront image and the first transmitted wavefront image, and a changing section which changes the first refractive index distribution data based on the first information to produce second refractive index distribution data. In the apparatus, the processing in the sections is repeated using the second refractive index distribution data as the first refractive index distribution data to produce the resulting second refractive index distribution data which is used as the output refractive index distribution data.

17 Claims, 14 Drawing Sheets

IMAGE PROCESSING APPARATUS AND REFRACTIVE INDEX DISTRIBUTION MEASURING APPARATUS

BACKGROUND OF THE INVENTION

The present invention relates to an image processing apparatus and a refractive index distribution measuring apparatus for providing an internal refractive index distribution of an object such as an optical element, and more particularly, to an apparatus for providing an internal refractive index distribution by analyzing a transmitted wavefront or interference fringes.

In recent years, optical elements such as lenses for use in digital cameras and laser-beam printers are often manufactured by molding of optical glass or plastic, and also, optical element shaving aspheric surfaces or free-form surfaces are often manufactured by molding. The molding enables processing of aspheric surfaces at low cost, but produces a nonuniform refractive index distribution within an optical element resulting from a molding time or a molding pressure in manufacture. The presence of the nonuniform refractive index distribution significantly affects the image-forming ability and the like of the optical element which requires high optical performance, so that design values cannot be achieved. Based on that fact, the measurement of the refractive index distribution is an important issue and high-accuracy measurement is needed.

In general, the measurement of a transmitted wavefront with an interferometer is widely used as a method of measuring a refractive index distribution. In conventional methods, however, only a refractive index distribution obtained from integration in a transmission direction of light is observed, and a three-dimensional refractive index distribution such as an internal distribution cannot be provided. To determine the three-dimensional distribution, an optical element to be tested must be measured in several parts, for example by slicing it, and high-accuracy measurement is difficult to achieve.

To solve the problem, Japanese Patent No. 3423486 has disclosed a method in which an object under test is immersed in matching oil having substantially the same refractive index as that of the object under test, and while the object under test is rotated around an axis orthogonal to the optical axis of a wave for test, transmitted wavefronts are measured successively, and an internal distribution is estimated in the cross section of the wave for test from the images of the transmitted wavefronts by performing CT (Computerized Tomography) analysis.

However, the change from interference fringes to transmitted wavefronts involves problems such as an error in a dense part of the interference fringes and a phase jump, and thus accurate transmitted wavefronts cannot be provided in many cases. Particularly, since the CT analysis used in the method disclosed in Japanese Patent No. 3423486 described above utilizes the Fourier transform, it cannot be performed if the images of transmitted wavefronts have any loss due to the abovementioned problems, an opaque part of the object under test, and the like. In addition, the measurement direction of the transmitted wavefronts is limited to one orthogonal to the axis around the single axis, so that it is difficult to provide a stable and accurate refractive index distribution.

Furthermore, in the wavefronts changed from the interference fringes, each pixel has a different expected error amount, but the difference in the error amount for each pixel cannot be reflected in the estimation of the refractive index distribution, leading to a reduction in accuracy.

BRIEF SUMMARY OF THE INVENTION

It is an object of the present invention to provide an image processing apparatus, an image processing program, and a refractive index distribution measuring apparatus, which impose no limitations on the measurement direction of transmitted wavefronts or interference fringes, have resistance to loss of a transmitted wavefront image and noise, and allows production of refractive index distribution data with high accuracy.

According to one aspect, the present invention provides an image processing apparatus which uses a first transmitted wavefront image measured by applying light to an object in each of a plurality of directions to produce output refractive index distribution data showing a refractive index distribution within the object.

The image processing apparatus has a simulating section which simulates a transmitted wavefront in each of the directions to produce a second transmitted wavefront image based on first refractive index distribution data, a comparing section which compares the second transmitted wavefront image with the first transmitted wavefront image to produce first information indicating the comparison result, and a changing section which changes the first refractive index distribution data based on the first information to produce second refractive index distribution data. The image processing apparatus repeats the processing in each of the sections using the second refractive index distribution data as the first refractive index distribution data and produces the resulting second refractive index distribution data as the output refractive index distribution data.

According to another aspect, the present invention provides an image processing apparatus which uses a first interference fringe image measured by an interferometer applying light to an object in each of a plurality of directions to produce output refractive index distribution data showing a refractive index distribution within the object.

The image processing apparatus has a simulating section which simulates the process of producing interference fringes by the interferometer to produce a second interference fringe image based on first refractive index distribution data, a comparing section which compares the second interference fringe image with the first interference fringe image to produce first information indicating the comparison result, and a changing section which changes the first refractive index distribution data based on the first information to produce second refractive index distribution data. The image processing apparatus repeats the processing in each of the sections using the second refractive index distribution data as the first refractive index distribution data and produces the resulting second refractive index distribution data as the output refractive index distribution data.

According to another aspect, the present invention provides an image processing program which uses a first transmitted wavefront image measured by applying light to an object in each of a plurality of directions to produce output refractive index distribution data showing a refractive index distribution within the object.

The program has a simulating step which simulates a transmitted wavefront in each of the directions to produce a second transmitted wavefront image based on first refractive index distribution data, a comparing step which compares the second transmitted wavefront image with the first transmitted wavefront image to produce first information indicating the comparison result, and a changing step which changes the first refractive index distribution data based on the first information to produce second refractive index distribution data. The image processing program repeats the processing in each of the steps using the second refractive index distribution data as the first refractive index distribution data and produces the resulting second refractive index distribution data as the output refractive index distribution data.

According to another aspect, the present invention provides an image processing program which uses a first interference fringe image measured by an interferometer applying light to an object in each of a plurality of directions to produce output refractive index distribution data showing a refractive index distribution within the object. The image processing apparatus has a simulating step which simulates the process of producing interference fringes by the interferometer to produce a second interference fringe image based on first refractive index distribution data, a comparing step which compares the second interference fringe image with the first interference fringe image to produce first information indicating the comparison result, and a changing step which changes the first refractive index distribution data based on the first information to produce second refractive index distribution data. The image processing program repeats the processing in each of the steps using the second refractive index distribution data as the first refractive index distribution data and produces the resulting second refractive index distribution data as the output refractive index distribution data.

In addition, a refractive index distribution measuring apparatus which has the abovementioned image processing apparatus and an interferometer taking the first transmitted wavefront image or the first interference fringe image forms one aspect of the present invention.

Other objects or features of the present invention will be apparent from the following description of preferred embodiments with reference to the drawings.

DETAILED DESCRIPTION OF THE PREFERRED EMBODIMENTS

Preferred embodiments of the present invention will hereinafter be described with reference to the drawings.

Embodiment 1

In an image processing apparatus and an image processing program of Embodiment 1, transmitted wavefront images (hereinafter referred to simply as transmitted wavefronts) formed by measuring an object under test (a physical object) in a plurality of light ray directions are used to produce refractive index distribution data (hereinafter referred to simply as a refractive index distribution) within the object.

Figure 1:
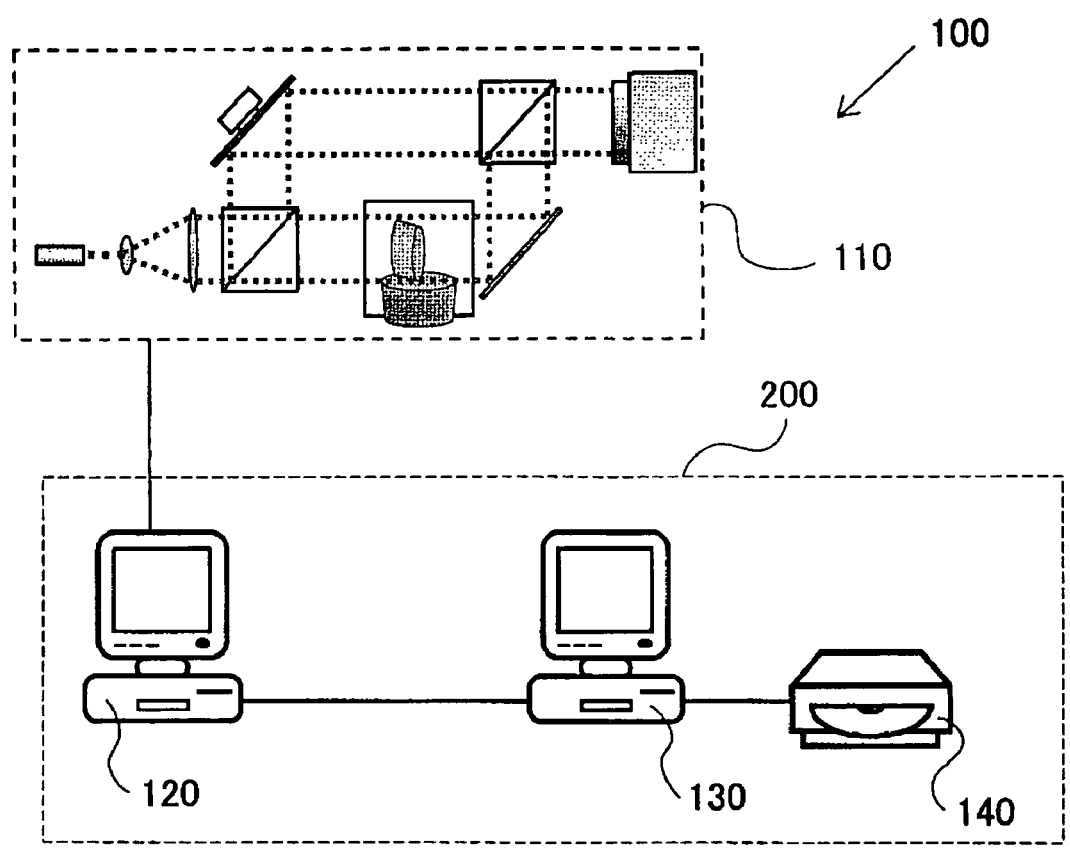
FIG. 1 shows the structure of a refractive index distribution measuring apparatus which is Embodiment 1 of the present invention.

FIG. 1 shows an example of the structure of a refractive index distribution measuring apparatus 100 which includes an image processing apparatus and an interferometer according to Embodiment 1. The refractive index distribution measuring apparatus 100 is comprised of an interferometer 110 and an image processing apparatus 200. The image processing apparatus 200 is comprised of a transmitted wavefront generator 120, a refractive index distribution generator 130, and a refractive index distribution recorder 140. The transmitted wavefront generator 120 and the refractive index distribution generator 130 are formed of separate personal computers. The respective components which constitute the interferometer 110 and the image processing apparatus 200 are formed such that they can communicate data with each other through a bus interface or the like. However, it is possible that the image processing apparatus 200 is formed of a single computer or that the transmitted wavefront generator 120 and the refractive index distribution generator 130 or the refractive index distribution generator 130 and the refractive index distribution recorder 140 are formed of a single computer and the other is formed of another computer.

Embodiment 1 is described in conjunction with the refractive index distribution measuring apparatus which includes the interferometer 110, the transmitted wavefront generator 120, and the refractive index distribution generator 130 as the components, but it is possible that the interferometer 110 and the transmitted wavefront generator 120 are provided as an apparatus separate from the refractive index distribution measuring apparatus which is formed to perform only a change from transmitted wavefronts to a refractive index distribution. In this case, the transmitted wavefronts taken and processed by the interferometer and the transmitted wavefront generator 120, which are separate from the refractive index distribution measuring apparatus, and then stored on a recording medium such as a semiconductor memory and a magnetic/optical disk may be read (input) by the refractive index distribution measuring apparatus. It is also possible to perform both of such reading of the transmitted wavefronts through the recording medium and direct reading of the transmitted wavefronts from the interferometer 110 and the transmitted wavefront generator 120.

In addition, Embodiment 1 is described in conjunction with the refractive index distribution measuring apparatus which includes the refractive index distribution recorder 140 as the component, but the refractive index distribution recorder 140 may be provided separately from the refractive index distribution measuring apparatus.

The interferometer 110 is formed to allow observation of interference fringes obtained by applying light to an object O under test such as a lens in a plurality of different directions (in other words, interference fringes formed by applying light in each of the plurality of directions).

Figure 2:
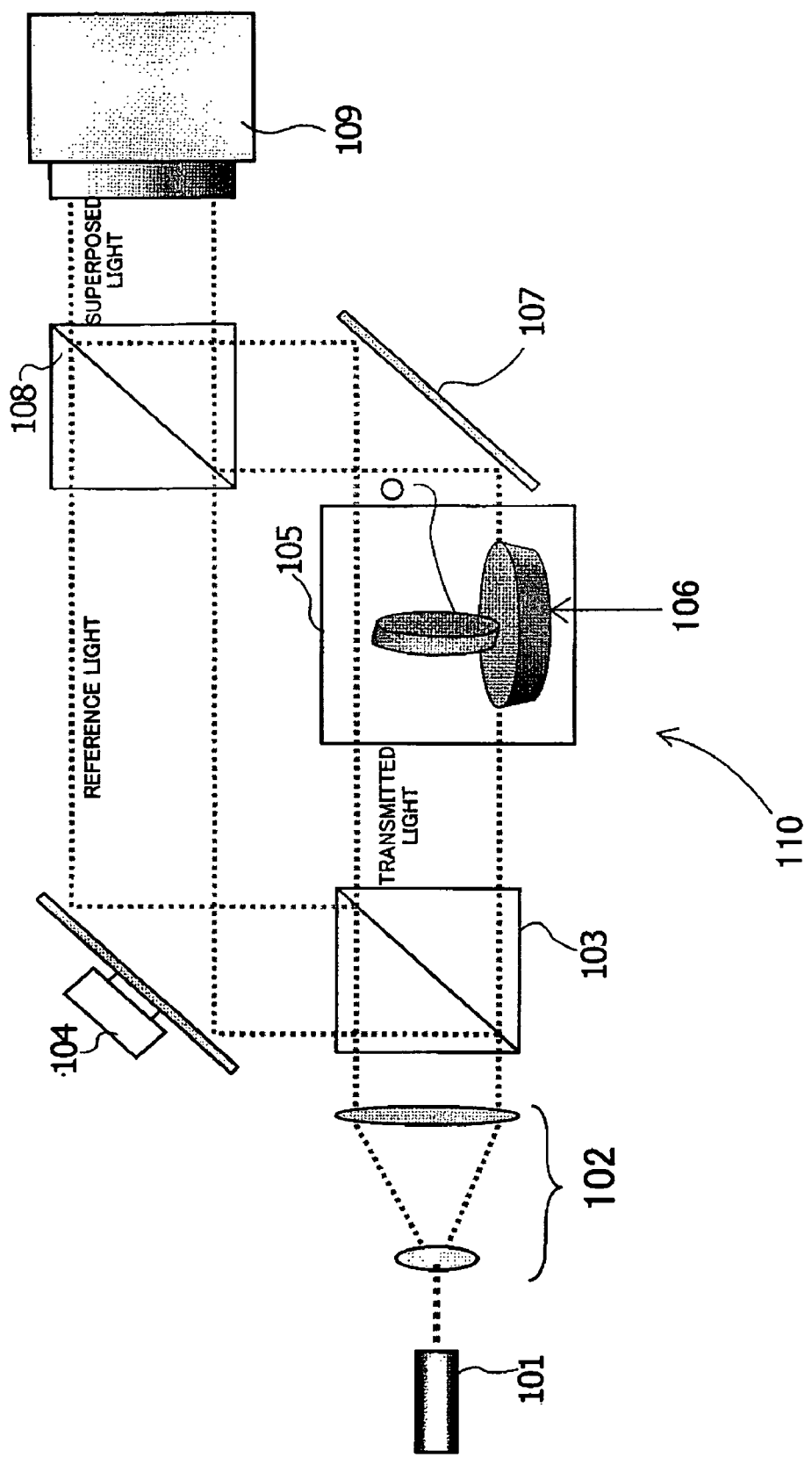
FIG. 2 shows the structure of an interferometer used in the refractive index distribution measuring apparatus of Embodiment 1.

As shown, for example in FIG. 2, the interferometer 110 is a so-called two-beam interferometer which is comprised of a laser light source 101 which emits coherent light, a beam expander 102 which increases the diameter of the laser light, a beam splitter 103 which splits the laser light into transmitted light and reference light, a piezoelectric mirror 104 which changes the optical path length of the reference light in the order of subwavelength, a matching bath 105 which contains the object O immersed in a matching liquid, a rotation mechanism 106 which changes the orientation of the object O in the matching bath 105, a reflecting mirror 107 which reflects the transmitted light passed through the object O, a beam splitter 108 which superposes the transmitted light on the reference light, and an image-taking apparatus 109 which takes the image of interference fringes formed from the superposed light.

FIG. 2 shows the object O for explanation, but the object O is not a component of the apparatus.

A laser beam emitted from the laser light source 101 is passed through the expander 102 which increases its diameter to encompass the object O. The beam is incident on the beam splitter 103 and split into transmitted light directed toward the object O and reference light to reach the image-taking apparatus 109 without passing through the object O. The transmitted light split by the beam splitter 103 passes through the matching bath 105 which contains the object O and is incident on the beam splitter 108 through the reflecting mirror 107. The reference light split by the beam splitter 103 is reflected by the piezoelectric mirror 104 and incident on the beam splitter 108 not through the object O (without passing through it). The transmitted light and the reference light incident on the beam splitter 108 are superposed by the beam splitter 108. The superposed laser light is incident on the image-taking apparatus 109. The image-taking apparatus 109 records (takes) the image of interference fringes, which is an image showing the intensity of the incident light in the cross section.

For measuring the interference fringes, the object O is set on the rotation mechanism 106 in the matching bath 105 which is filled with the liquid (the matching liquid) having substantially the same refractive index as that of the object O. The rotation mechanism 106 is driven to change the orientation of the object O to cause the light ray to be incident on the object O in a plurality of directions, and the image of the interference fringes is taken in each of the plurality of light ray directions.

The matching bath 105 has light incidence/emergence parts formed of transparent flat plates disposed in parallel. Since the matching bath 105 is filled with the matching liquid having substantially the same refractive index as that of the object O, the transmitted light passes through the matching bath 105 with almost no refraction. However, if the object O has variations (unevenness) in refractive index inside, the variations are integrated in the light ray direction as a difference in optical path length to result in fluctuations in the wavefront of the light which emerges from the matching bath 105. The transmitted light having the fluctuations is superposed on the reference light to present the interference fringes showing the intensity of the superposed light in the cross section, and the image of the interference fringes is taken by the image-taking apparatus 109. The taken image is output as a measured interference fringe image.

The transmitted wavefront generator 120 produces a measured transmitted wavefront (a first transmitted wavefront image) by performing image processing in each of the light ray directions in the measured interference fringe image (hereinafter referred to simply as measured interference fringes) provided by the interferometer 110. The image processing performed at this point will be described later, but an existing processing method for analysis of interference fringes may be used.

The refractive index distribution generator 130 collectively processes the measured transmitted wavefronts for the respective light ray directions produced by the transmitted wavefront generator 120 to produce a refractive index distribution within the object O (output refractive index distribution data). The refractive index distribution is three-dimensional volume data which shows how the refractive index is distributed within the object O, in which the error is at the minimum between the measured transmitted wavefronts and estimated transmitted wavefronts which are presumably provided if the object O has such a refractive index distribution and is measured in a similar manner to that with the interferometer 110. In addition, the refractive index distribution has a natural (that is, continuous) distribution. The method of producing the internal refractive index distribution will be described later in detail.

The refractive index distribution recorder 140 stores the refractive index distribution produced by the refractive index distribution generator 130 on various types of recording media described above. The stored refractive index distribution may be used for optical design, molding evaluation, or the like.

Description will hereinafter be made of the more detailed structure and operation of each component of the refractive index distribution measuring apparatus 100. In the interference fringe measurement, while the object O is set on the rotation mechanism 106 of the interferometer 110, the piezoelectric mirror 104 is driven for a rotation position $R_i$ of the rotation mechanism 106, and images of interference fringes at a plurality of reference light phases $\theta_{ij}$ are taken by the image-taking apparatus 109. The number of the reference light phases used for one rotation position $R_i$ depends on the processing method in the transmitted wavefront generator 120, and in Embodiment 1, four reference light phases $\{\theta_{i1}, \theta_{i2}, \theta_{i3}, \theta_{i4}\}=\{0, \pi/2, \pi, -\pi/2\}$ are used in image-taking for any of rotation positions.

After the completion of the image-taking at four reference light phases for one rotation position $R_i$, the rotation mechanism 106 is operated to set the object O to another rotation position $R_{i+1}$ and image-taking is performed similarly at four reference light phases. The number of rotation positions for taking images depends on the ultimately required resolution or accuracy of a refractive index distribution.

Figure 14:
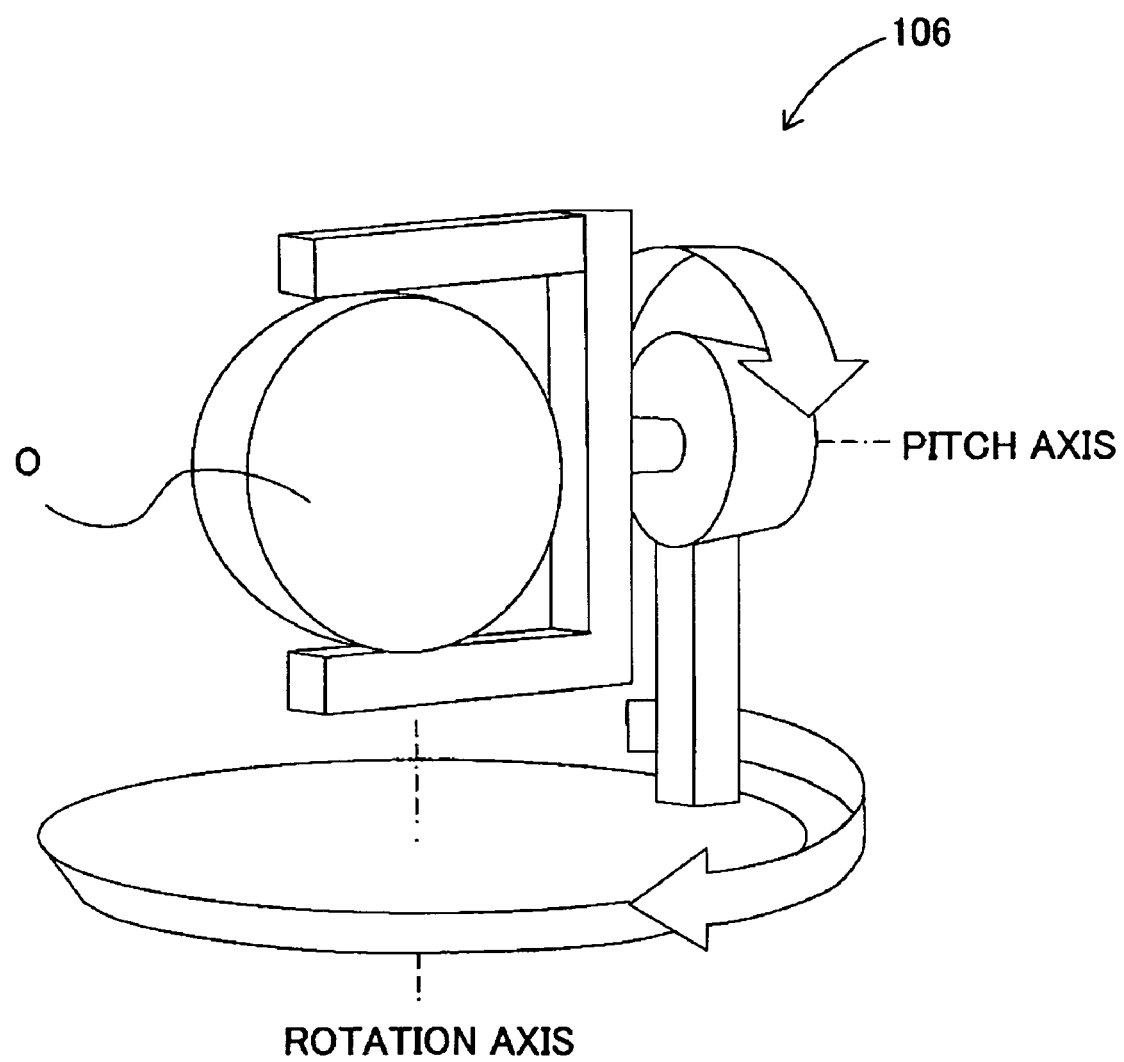
FIG. 14 is a schematic diagram showing the structure of a rotation mechanism used in the interferometer of Embodiments 1 to 5.

As shown in FIG. 14, the rotation mechanism 106 desirably has a plurality of rotation axes such as a rotation axis and a pitch axis, and the rotation position $R_i$ is represented by a three-dimensional rotation angle as in quarternions, not by a single rotation angle. A series of rotation positions $\{R_i\}$ is arranged to have various rotation angles around each axis.

The measured interference fringes F thus taken as images can be expressed with each rotation position $R_i$ and reference light phase $\theta_{ij}$ as follows:

$F(R_i, \theta_{ij}, x, y)$ where x and y represent coordinates on the image. The measured interference fringes F taken as images are input to the transmitted wavefront generator 120.

Figure 3:
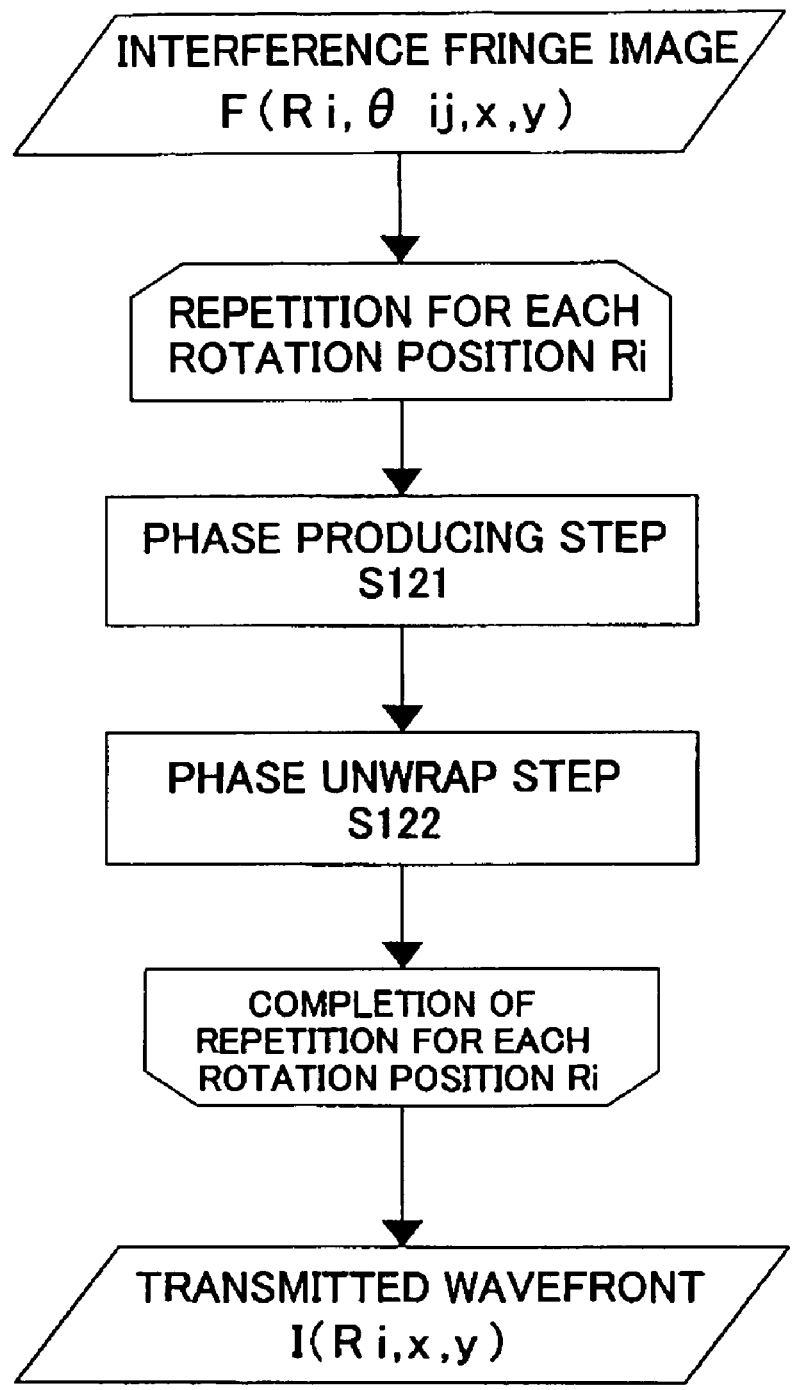
FIG. 3 is a flow chart showing the operation of a transmitted wave generator which forms part of the refractive index distribution measuring apparatus of Embodiment 1.

The transmitted wavefront generator 120 receives the measured interference fringes $F(R_i, \theta_{ij}, x, y)$ from the interferometer 110 and calculates a measured transmitted wavefront $I(R_i, x, y)$ at each rotation position $R_i$. The processing at this point is classified into a phase producing step S121 and a phase unwrap step S122 as shown in a flow chart of FIG. 3.

It should be noted that each operation step in the transmitted wavefront generator 120 and the refractive index distribution generator 130 is performed by an image processing program as a computer program, but each step may be regarded as a section to allow the transmitted wavefront generator 120 and the refractive index distribution generator 130 to serve as the image processing apparatus having those sections. When the transmitted wavefront generator 120 and the refractive index distribution generator 130 are implemented as a computer program, operation steps associated with the two generators 120 and 130 may be performed on a single computer. This applies to other embodiments later described.

First, the transmitted wavefront generator 120 takes a group of images at different reference light phases $\theta_{ij}$ for each rotation position $R_i$. In Embodiment 1, the four phases expressed by:

$\{\theta_{i1}, \theta_{i2}, \theta_{i3}, \theta_{i4}\} = \{0, \pi/2, \pi, -\pi/2\}$ are used to produce four images expressed by:

$\{F_1 = F(R_i, 0, x, y), F_2 = F(R_i, \pi/2, x, y), F_3 = F(R_i, \pi, x, y), F_4 = F(R_i, -\pi/2, x, y)\}$.

At the phase production step S121, a wrapped phase image $I'(R_i, x, y)$ is produced from the group of images as follows:

$$I' = \begin{cases} \tan^{-1}\left(\frac{F_2 - F_4}{F_1 - F_3}\right) & \text{for } F_1 - F_3 \geq 0 \\ \tan^{-1}\left(\frac{F_2 - F_4}{F_1 - F_3}\right) - \pi & \text{for } F_1 - F_3 < 0 \end{cases} \quad (1)$$

to satisfy:

$-\pi \leq I'(R_i, x, y) < \pi$.

In the above expression, the range of values of $\tan^{-1}$ is set to $(0, \pi)$.

When the standard deviation of the measurement errors estimated in the interference fringe image F is assumed to be a certain value $\sigma_F$, the standard deviation $\sigma_{I'}$ of the errors in I' is expressed by:

$$\sigma_{I'} = \sqrt{2}\sqrt{\left(\frac{\cos^2 I'}{F_2 - F_4}\right)^2 + \left(\frac{\sin^2 I'}{F_1 - F_3}\right)^2} \quad (2)$$

so that $\sigma_{I'}$ may be significantly large when the transmitted light is faint or in a pixel in which F2 and F4 or F1 and F3 have close measurement values due to noise in the image-taking apparatus 109.

In the wrapped phase image I' thus obtained, the phase may jump from near $+\pi$ to $-\pi$ in adjacent pixels even in areas where the image is smoothly changed actually. Such a phenomenon is called wrapping. Thus, at the next phase unwrap step S122, phase unwrap is performed to solve the problem. In the phase unwrap, when the difference in the value of the wrapped phase image I' between two adjacent pixels $(x_1, y_1)$, $(x_2, y_2)$ in the interference fringe image expressed by:

$|I'(R_i, x_1, y_1) - I'(R_i, x_2, y_2)|$ is larger than $\pi$, $2n\pi$ (n is an integer number) is added to or subtracted from one of the images to adjust the difference in phase between the adjacent pixels to $\pi$ or smaller. At this point, the zero point is set in an area of the image where the object O is not present.

The transmitted wavefront generator 120 inputs the image thus adjusted to the refractive index distribution generator 130 as the measured transmitted wavefront $I(R_i, x, y)$.

The transmitted wavefront generator 120 may produce an area in which the transmitted wavefront image I cannot appropriately be determined due to noise on the measured interference fringes F, the excessively thick interference fringes, or the shadow of the rotation mechanism 106. The area is not filled with the wavefront values by interpolation from the surrounding values, and the refractive index distribution generator 130 is notified that the wavefront in that area is undetermined, for example by setting the wavefront values to "Not a Number" (NaN).

The refractive index distribution generator 130 estimates a three-dimensional refractive index distribution N (u, v, w) of the object O from the measured transmitted wavefront I $(R_i, x, y)$ of the object O measured in the plurality of light ray directions (that is, the rotation positions). It should be noted that (u, v, w) represent a rectangular coordinate system fixed on the object O.

Figure 4:
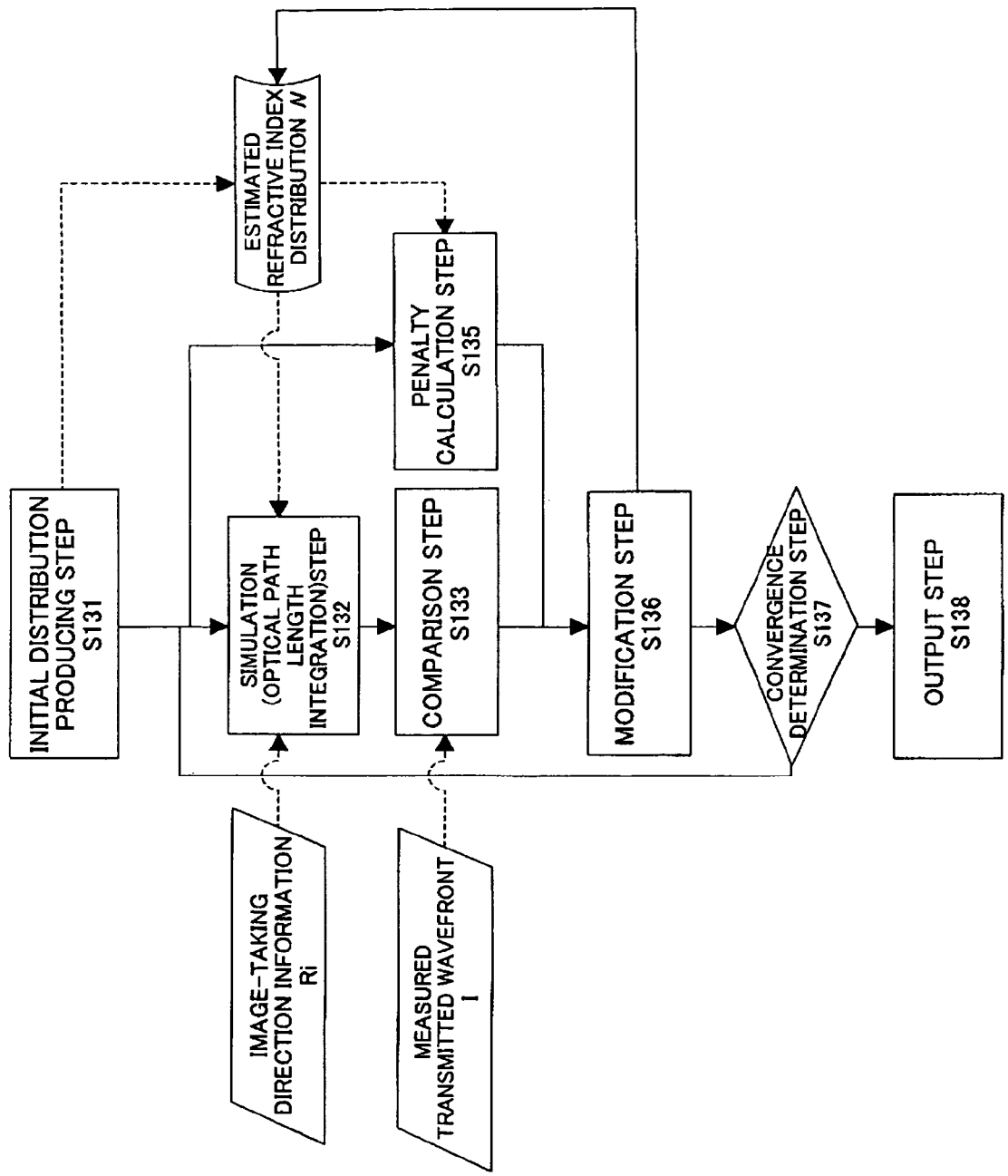
FIG. 4 is a flow chart showing the operation of a refractive index distribution generator which forms part of the refractive index distribution measuring apparatus of Embodiment 1.

The operation of the refractive index distribution generator 130 will be described with reference to a flow chart of FIG. 4. The processing of the refractive index distribution generator 130 is comprised of an initial distribution producing step S131, a simulation (optical path length integration) step S132, a comparison step S133, a penalty calculation step S135, a modification (change) step S136, a convergence determination step S137, and an output step S138. Of them, the simulation step S132 to the convergence determination step S137 form a repetitive loop which is repeated over a plurality of times.

The refractive index distribution generator 130 receives as input data the measured transmitted wavefront $I(R_i, x, y)$ (the first transmitted wavefront image) and the information of the rotation position (image-taking direction) Ri of the object O at the time of taking each transmitted wavefront and holds as a variable an estimated refractive index distribution N(u, v, w).

First, at the initial distribution producing step S131, the refractive index distribution generator 130 produces an initial distribution $N^0$ of an estimated refractive index distribution $N''$ (first refractive index distribution data). In this case, the estimated refractive index distribution $N''$ is expressed, for example, in voxels which are defined by dividing the space of (u, v, w) into 1-mm parts for representing the refractive index of each part. Since the initial estimated refractive index distribution $N^0$ produced at this step does not affect the finally produced output refractive index distribution, any refractive index distribution may be used, and for example, a constant value expressed by:

$$N^0(u, v, w)=0$$

is used.

At the simulation step S132, the refractive index distribution generator 130 produces an estimated transmitted wavefront $I''$ (a second transmitted wavefront image) which is presumably provided if the estimated refractive index distribution $N''$ is the refractive index distribution N of the object O. To this end, the following:

$$I''(R_i, x, y) = \int N''\{u(R_i, x, y, z), v(R_i, x, y, z), w(R_i, x, y, z)\}dz \quad (3a)$$

$$\begin{pmatrix} u(R_i, x, y, z) \\ v(R_i, x, y, z) \\ w(R_i, x, y, z) \end{pmatrix} = Rot(R_i)^{-1} \begin{pmatrix} x \\ y \\ z \end{pmatrix} \quad (3b)$$

is used in consideration of the rotation position $R_i$ at the measurement of the interference fringes, that is, the light ray directions. Specifically, the estimated refractive index distribution $N''$ in each light ray direction (in other direction, the optical path direction) is integrated with the expression (3) to calculate the estimated transmitted wavefront $I''$. Then, the optical path direction is determined by coordinate transformation with the expression (3b). In the expression (3b), Rot ($R_i$) represents a three-dimensional rotating matrix which expresses the rotation position $R_i$ and indicates transformation from the coordinate system (u, v, w) fixed on the object O to the coordinate system (x, y, z) fixed on the interferometer 110.

The estimated transmitted wave $I''$ is expressed as a determinant $I''=AN''$ when vector expressions of $N''$ and $I''$ are used, where A represents a system matrix indicating projective transformation. The vector expression is provided by replacing $N''$ (u, v, w) and $I''(R_i, x, y)$ with a one-dimensional vector $\{N''_{u,v,w}\}$ and $\{I''_{Ri, x, y}\}$.

At the comparison step S133, the refractive index distribution generator 130 compares the estimated transmitted wavefront $I''$ provided at the simulation step S132 with the measured transmitted wavefront I (the first transmitted wavefront image) actually provided by the interferometer 110 and the transmitted wavefront generator 120 and inputs the difference between them expressed by:

$$d''(R_i, x, y)=I(R_i, x, y)-I''(R_i, x, y)$$

as an estimated error (first information) to the modification step S136. For the area of the transmitted wavefront image I where the wavefront values cannot be determined appropriately, the value of d for that area is set to zero.

On the other hand, at the penalty calculation step S135, the refractive index distribution generator 130 calculates a small modification amount $\{\delta N''|P(N''+\delta N'')>P(N'')|\}$ (second information) to increase a penalty function $P(N'')$ defined for the estimated refractive index distribution, and inputs the amount to the modification step S136.

The penalty function represents the "unnaturalness" (or discontinuity) of the refractive index distribution $N''$. For example, the refractive index distribution is assumed to be a continuous one, and the penalty function $P(N'')$ is defined as follows:

$$P(N'')=(\Delta N'')^2$$

which is the square norm of a spatial variation $\nabla N''$ of $N''$, and the gradient is defined as follows:

$$\delta N''=\nabla P(N'')=\nabla N''$$

This is expressed in a discrete system as follows:

$$P(N^n) = (\nabla N^n)^2$$
$$= \sum_{u,v,w} N^n(u, v, w)\{6N^n(u, v, w) - N^n(u+1, v, w) - N^n(u-1, v, w) - N^n(u, v+1, w) - N^n(u, v-1, w) - N^n(u, v, w+1) - N^n(u, v, w-1)\}$$

$$\delta N^n = \Delta N^n$$
$$= \sum_{u,v,w} 2\{6N^n(u, v, w) - N^n(u+1, v, w) - N^n(u-1, v, w) - N^n(u, v+1, w) - N^n(u, v-1, w) - N^n(u, v, w+1) - N^n(u, v, w-1)\}$$

and a partial penalty is calculated only depending on the refractive index N of the associated part (u, v, w) and the close parts (u+1, v, w), (u−1, v, w), (u, v+1, w), (u, v−1, w), (u, v, w+1), (u, v, w−1), and expressed by:

$$p(u, v, w) = N^n(u, v, w)\{6N^n(u, v, w) - N^n(u+1, v, w) - N^n(u-1, v, w) - N^n(u, v+1, w) - N^n(u, v-1, w) - N^n(u, v, w+1) - N^n(u, v, w-1)\}.$$

With that partial penalty, the penalty is expressed as the sum of them as:

$$P(N'')=\Sigma_{u, v, w}p(u, v, w).$$

At the modification step S136, the refractive index distribution generator 130 modifies (changes) the estimated refractive index distribution $N''$ based on the estimated error $d''$ provided at the comparison step S133 and the small modification amount $\delta N''$ provided at the penalty calculation step S135. To this end, first, the difference $d''(R_i, x, y)$ on the transmitted wavefront image space $(R_i, x, y)$ provided at the comparison step S133 is divided by the standard deviation $\sigma_I(R_i, x, y)$ of the error expected in the transmitted wavefront before transformation into a value $e''$ (u, v, w) on the object coordinate space (u, v, w). This makes a pair with the transformation from the estimated refractive index distribution $N''$ to the estimated transmitted wavefront $I''$ at the simulation step S132 expressed by:

$$I''=AN''$$

and is inverse projection expressed by the following expression (4):

$$e^n(u, v, w) = \sum_i \frac{d^n(R_i, x(R_i, u, v, w), y(R_i, u, v, w))}{\sigma_I(R_i, x(R_i, u, v, w), y(R_i, u, v, w))} \Big/ \text{depth} \quad (4)$$

$$\begin{pmatrix} x(R_i, u, v, w) \\ y(R_i, u, v, w) \\ * \end{pmatrix} = Rot(R_i) \begin{pmatrix} u \\ v \\ w \end{pmatrix}$$

This can be described as the following determinant by using the vector representation of $d^n$ and $e^n$:

$$e^n = A^t d^n.$$

While "depth" in the expression (4) represents a distance over which the object O is passed by the transmitted light measured as the transmitted wavefront $I(R_i, \theta, x, y)$ at the measurement of the interference fringes, it does not necessarily require an accurate value, and a fixed value of a typical or representative thickness of the object may be used. Then, the estimated refractive index distribution N is modified as:

$$N^{n+1} = N^n + \mu(e^n - \beta \delta N^n)$$

and the result is set to a new estimated refractive index distribution $N^{n+1}$ (second refractive index distribution data). In the abovementioned expression, µ represents a parameter indicating a step in successive approximation and takes the value defined as:

$$0 < \mu/\sigma_I(R_i, x, y) < 2.$$

At the convergence determination step S137, the convergence of the successive approximation is determined. If converged, the flow proceeds to the output step S138, or to the simulation step S132 and the penalty calculation step S135 if not converged. If it is not converged, the estimated refractive index distribution input at the simulation step S132 and the penalty calculation step S135 is the estimated refractive index distribution newly produced in the modification at the modification step S136.

For the method of determining whether the convergence is achieved or not, the determination may be made when the norm $\beta|e^n - \beta \delta N^n|$ of the modification amount at the modification step S136 is lower than a predetermined threshold value or larger than the norm $\beta|e^{n-1} - \beta \delta N^{n-1}|$ of the previous modification amount. In addition, the convergence may be determined when the repetition of the processing reaches a predetermined number or the processing time reaches a predetermined time.

In the repetitive loop, each time the estimated refractive index distribution N is changed at the modification step S136, the estimated error d and the penalty P(N) are evaluated, and the distribution N is changed such that the value expressed by:

$$\left(\frac{d}{\sigma_I}\right)^2 + \beta P(N) \quad (5)$$

is reduced.

At the output step S138, the estimated refractive index distribution $N^m$ at that point is output as a value produced by the refractive index distribution generator 130 (output refractive index distribution data) N. The final refractive index distribution N is provided to minimize the value expressed by:

$$\left(\frac{d}{\sigma_I}\right)^2 + \beta P(N) \quad (6)$$

Since N output from the refractive index distribution generator 130 is a relative value of the phase change amount per unit length to the matching liquid, transformation thereof to a refractive index in a standard unit requires the following calculation:

$$N = \frac{\lambda}{2\pi} N + N_0 \quad (7)$$

where λ represents the wavelength of the laser light, and $N_0$ represents the refractive index of the matching liquid.

The refractive index distribution recorder 140 records the refractive index distribution N produced by the refractive index distribution generator 130. The representation form of the output may be a list of the refractive indexes N (u, v, w) of the respective voxels or a list as approximate coefficients $A_i$ in a polynomial approximation expressed by:

$$N(u, v, w) \approx A_0 + A_1 u + A_2 v + A_3 w + A_4 u^2 + A_5 v^2 + A_6 w^2 + A_7 u v + A_8 v w + A_9 w u + \quad (8)$$

In addition, it may be a list of Fourier series or fitting coefficients in a fitting function such as a Zernike polynomial.

As described above, the refractive index distribution generator 130 of Embodiment 1 combines the correction with the difference between the estimated transmitted wavefront and the measured transmitted wavefront provided at step S132 and step S133 with the correction by the penalty function provided at step S135 and repetitively uses the combined correction to minimize both of the error the penalty function. This allows the production and output of the refractive index distribution N with high-definition and less noise, that is, high accuracy, based on the transmitted wavefronts measured in the plurality of light ray directions, not limited to a single rotation axis.

Embodiment 2

In an image processing apparatus and an image processing program of Embodiment 2, refractive index distribution data (hereinafter referred to simply as a refractive index distribution) within an object under test is produced directly from an interference fringe image (hereinafter referred to as measured interference fringes) provided by measuring the object under test in a plurality of light ray directions.

Figure 5:
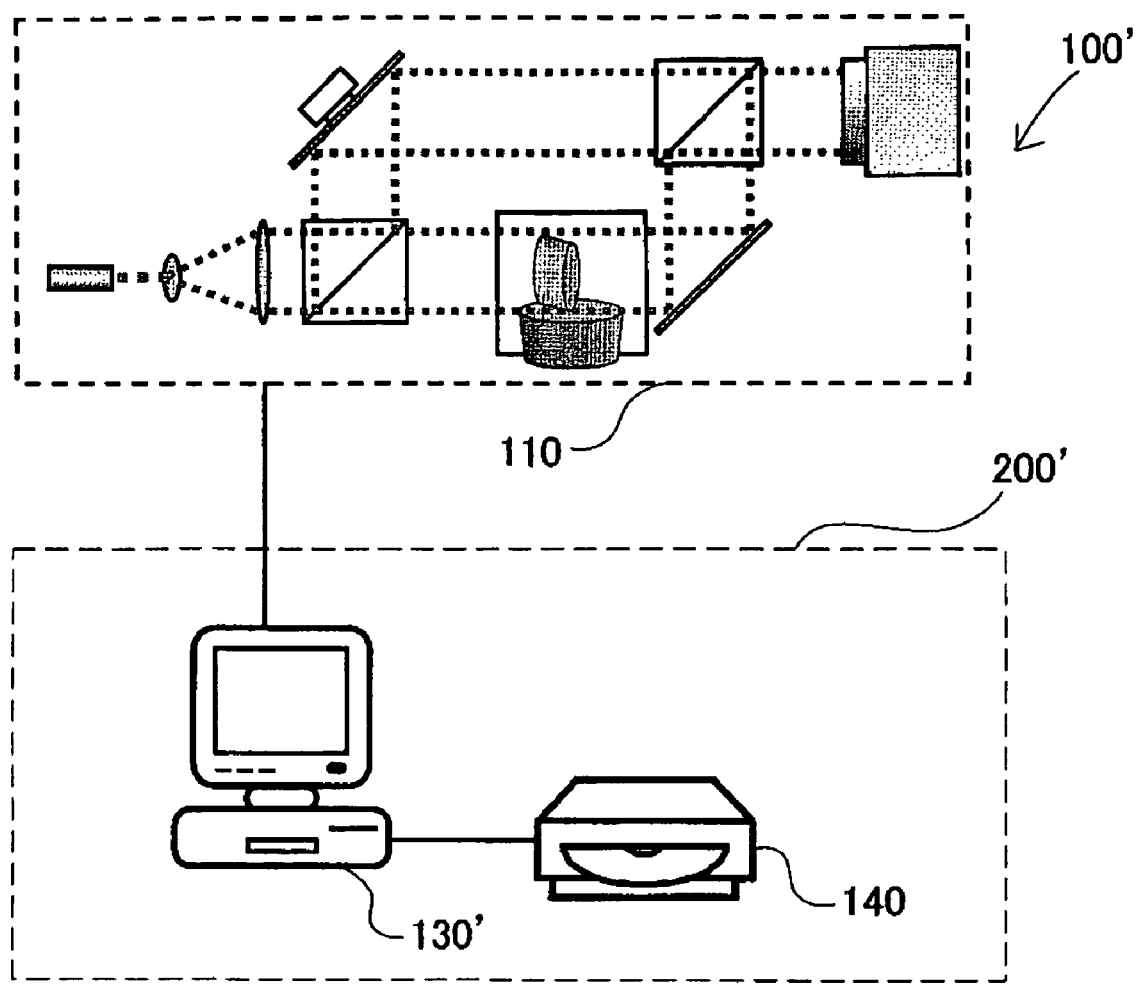
FIG. 5 shows the structure of a refractive index distribution measuring apparatus which is Embodiment 2 of the present invention.

FIG. 5 shows an example of the structure of a refractive index distribution measuring apparatus 100' which includes the image processing apparatus and an interferometer of Embodiment 2. The refractive index distribution measuring apparatus 100' is comprised of an interferometer 110 and an image processing apparatus 200'. The image processing apparatus 200' is comprised of a refractive index distribution generator 130' and a refractive index distribution recorder 140. The refractive index distribution generator 130' is formed of a single personal computer. The respective components which constitute the interferometer 110 and the image processing apparatus 200' are formed such that they can communicate data with each other through a bus interface, for example.

The interferometer 110 and the refractive index distribution recorder 140 are similar to those in Embodiment 1, but in Embodiment 2, the transmitted wavefront generator 120 used in Embodiment 1 is not provided. Measured interference fringes provided by the interferometer 110 are directly input to the refractive index distribution generator 130' which then processes the measured interference fringes provided by the interferometer 110 to produce a refractive index distribution (output refractive index distribution data) within an object O under test. The refractive index distribution is three-dimensional volume data which shows how the refractive index is distributed within the object O, in which the error is at the minimum between the measured interference fringes and estimated interference fringes which are presumably provided if the object O has such a refractive index distribution and is measured in a similar manner to that with the interferometer 110. In addition, the refractive index distribution has a natural distribution. The method therefor will be described later in detail.

Next, description will hereinafter be made of the more detailed operation of each component of the refractive index distribution measuring apparatus 100'. In interference fringe measurement, while the object O is set on a rotation mechanism 106 of the interferometer 110, the rotation mechanism 106 and a piezoelectric mirror 104 are driven to take (record) an image of interference fringes at a rotation position $R_i$ and a reference light phase $\theta_i$ by an image-taking apparatus 109. The taken image is output as measured interference fringes.

After the image-taking is completed, the rotation mechanism 106 and the piezoelectric mirror 104 are operated to set the object O to another rotation position $R_{i+1}$ and another reference light phase $\theta_{i+1}$ and image-taking is repeated similarly. The number of rotation positions at which images are taken depends on the ultimately required resolution or accuracy in the refractive index distribution.

In Embodiment 2, it is unnecessary to take images of interference fringes at a plurality of reference light phases at each rotation position $R_i$ as in Embodiment 1, and it is only necessary to take the image of interference fringes at an arbitrary reference light phase $\theta_i$ at each rotation position $R_i$. Of course, the image-taking may be performed at a plurality of reference light phases $\theta_i$ at the same rotation position, but they are handled as images at different rotation positions $R_i$, $j$ with the same rotation angle ($R_i = R_j$). Alternatively, the reference light phase $\theta_i$ may be maintained constant by replacing the piezoelectric mirror 104 with a typical (fixed) mirror.

The measured interference fringes F thus taken as images can be expressed as $F(R_i, \theta_i, x, y)$ with each rotation position $R_i$ and reference light phase $\theta_i$, where x and y represent coordinates on the image. The taken images of the measured interference fringes F are input to the refractive index distribution generator 130'.

For simplify the description, it is assumed that the reference light and the transmitted light in the interferometer 110 have the equal intensity, and the intensity of the light superposed at the same phase is equal to one.

The refractive index distribution generator 130' estimates a three-dimensional refractive index distribution N(u, v, w) of the object O from the measured interference fringes $F(R_i, \theta_i, x, y)$ provided in the plurality of light ray directions. It should be noted that (u, v, w) represent a rectangular coordinate system fixed on the object O.

Figure 6:
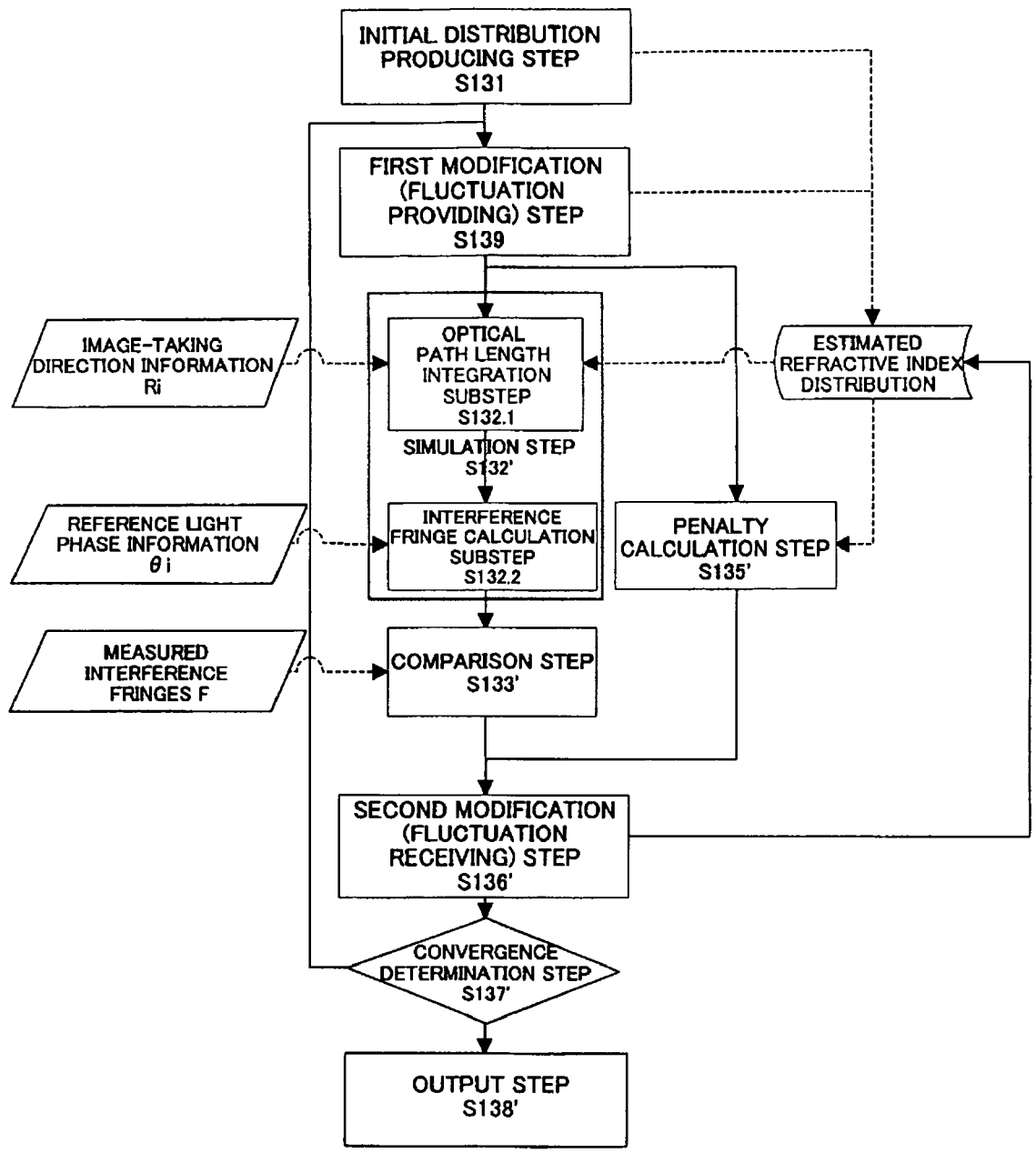
FIG. 6 is a flow chart showing the operation of a refractive index distribution generator which forms part of the refractive index distribution measuring apparatus of Embodiment 2.

The operation of the refractive index distribution generator 130' will be described with reference to a flow chart of FIG. 6. The processing of the refractive index distribution generator 130' is comprised of an initial distribution producing step S131, a first modification (fluctuation providing) step S139, a simulation step S132', a comparison step S133', a penalty calculating step S135', a second modification (fluctuation receiving) step S136', a convergence determination step S137', and an output step S138. Of them, the first modification step S139 to the convergence determination step S137' form a repetitive loop which is repeated over a plurality of times.

The refractive index distribution generator 130' receives as input data the measured interference fringes $F(R_i, \theta_i, x, y)$ and the information of the rotation position (image-taking direction) $R_i$ and the reference light phase $\theta_i$ at the time of taking the respective interference fringes and holds as a variable an estimated refractive index distribution N(u, v, w).

First, at the initial distribution producing step S131, the refractive index distribution generator 130' produces an initial distribution $N^0$ of an estimated refractive index distribution $N^n$ (first refractive index distribution data), similarly to Embodiment 1.

At the first modification step S139, the refractive index distribution generator 130' provides a random change for the estimated refractive index distribution $N^n$. This is performed for escaping from a stable state in a local optimal solution caused by the simulator in Embodiment 2 including nonlinear transformation.

The simulation step S132' is comprised of an optical path length integration substep S132.1 and an interference fringe calculation substep S132.2, in which the process of producing the interference fringes in the interferometer 110 is simulated to produce estimated interference fringes $F^n$.

At the optical path length integration substep S132.1, similarly to the simulation step S132 in Embodiment 1, the estimated refractive index distribution $N^n$ in each light ray direction (rotation position) is integrated to produce an estimated transmitted wavefront $I^n$ (a transmitted wavefront image).

At the interference fringe calculation substep S132.2, the estimated interference fringes $F^n$ are produced from the estimated transmitted wavefront $I^n$ produced at the optical path length integration substep S132.1. To this end, the following expression is used:

$$F^n(R_i, x, y) = \sqrt{\frac{1 + \cos(I^n(R_i, x, y) - \theta_i)}{2}} \qquad (9)$$

in consideration of the reference light phase $\theta_i$ (first reference wavefront data) at the time of interference fringe measurement.

At the comparison step S133', the refractive index distribution generator 130' compares the estimated interference fringes $F^n$ provided at the simulation step S132' with the measured interference fringes F actually provided by the interferometer 110 and inputs the difference $d^n(R_i, x, y) = F(R_i, x, y) - F^n(R_i, x, y)$ to the second modification (fluctuation receiving) step S136' as an estimated error (first information).

On the other hand, at the penalty calculation step S135', the refractive index distribution generator 130' calculates a penalty function $P(N'')$ defined for the estimated refractive index distribution $N''$. For example, it calculates the penalty as follows:

$$P(N'') = (\nabla N'')^2$$

similarly to Embodiment 1, and inputs the result to the second modification step S136'.

At the second modification step S136', the refractive index distribution generator 130 modifies (changes) the estimated refractive index distribution $N''$ based on the estimated error $d''$ provided at the comparison step S133' and the penalty $P(N'')$ provided at the penalty calculation step S135'. To this end, the refractive index distribution generator 130 compares the following:

$$E^n = \left(\frac{d^n}{\sigma_F}\right)^2 + \beta P(N^n) \tag{10}$$

which is the current evaluation value (second information) with the following:

$$E^{n-1} = \left(\frac{d^{n-1}}{\sigma_F}\right)^2 + \beta P(N^{n-1}) \tag{11}$$

which is the previous evaluation value. If the increase amount $\Delta E = E^n - E^{n-1}$ is a positive value, the refractive index distribution generator 130' returns the estimated refractive index distribution $N''$ to the value $N''^{-1}$ before the execution of the preceding first modification step 139 at the probability of $P = 1 - \exp(-\Delta E / T)$. T represents a control parameter having a positive value and is appropriately reduced as the process is repeated.

At the convergence determination step S137', the value of the control parameter T is referred to, and the flow proceeds to the output step S138 if the value of T is lower than a predetermined threshold, or to the first modification step S139 if not. At this point, the estimated refractive index distribution input to the first modification step S139 is the newly produced estimated refractive index distribution in the modification at the second modification step S136'.

In the repetitive loop, each time the estimated refractive index distribution N is changed at the first modification step S139, the estimated error d and the penalty P(N) are evaluated. Since the change provided at the first modification step S139 is random, the evaluation value expressed by:

$$E = \left(\frac{d}{\sigma_F}\right)^2 + \beta P(N) P(N) \tag{12}$$

may be reduced or increased. However, since the second modification step S136' reduces the probability that a change of increasing the evaluation value is accepted, the evaluation value E is gradually reduced as the process is repeated many times.

At the output step S138, the estimated refractive index distribution $N'''$ at that point is output as a final refractive index distribution (output refractive index distribution data) N of the refractive index distribution generator 130'. When the reduction in the control parameter T is sufficiently slow, the final refractive index distribution N is provided at a high probability to minimize the value expressed by:

$$\left(\frac{d}{\sigma_F}\right)^2 + \beta P(N) \tag{13}$$

similarly to Embodiment 1.

The abovementioned first and second modification steps S139, S136', and the convergence determination step S137' are typically based on an optimization algorithm called the Simulated Annealing. However, the modification step and the convergence determination step based on another optimization algorithm such as a genetic algorithm may also be introduced to provide N with the minimized value of the expression (13).

Similarly to Embodiment 1, since the final refractive index distribution N output from the refractive index distribution generator 130' is a relative value of the phase change amount per unit length to the matching liquid, transformation thereof to a refractive index in a standard unit requires the following calculation:

$$N = \frac{\lambda}{2\pi} N + N_0 \tag{14}$$

where $\lambda$ represents the wavelength of the laser light, and $N^0$ represents the refractive index of the matching liquid.

The refractive index distribution recorder 140 records the final refractive index distribution N produced by the refractive index distribution generator 130'.

According to Embodiment 2, since the production of the transmitted wavefronts from the phase fringes is not performed, the process is not affected by errors associated with the production of the transmitted wavefronts such as a phase jump and thus a more accurate refractive index distribution can be provided. In addition, the images of interference fringes do not need to be taken at a plurality of reference light phases at each rotation position, so that the same number of images can be taken at an increased number of rotation positions to achieve a refractive index distribution with higher spatial resolution.

Embodiment 3

The image processing method described in Embodiment 2 can be extended to address the case where the object O is made of glass material with partially low transmittance or the phase of reference light is uncertain. An image processing method which addresses these cases will hereinafter be described.

Figure 7:
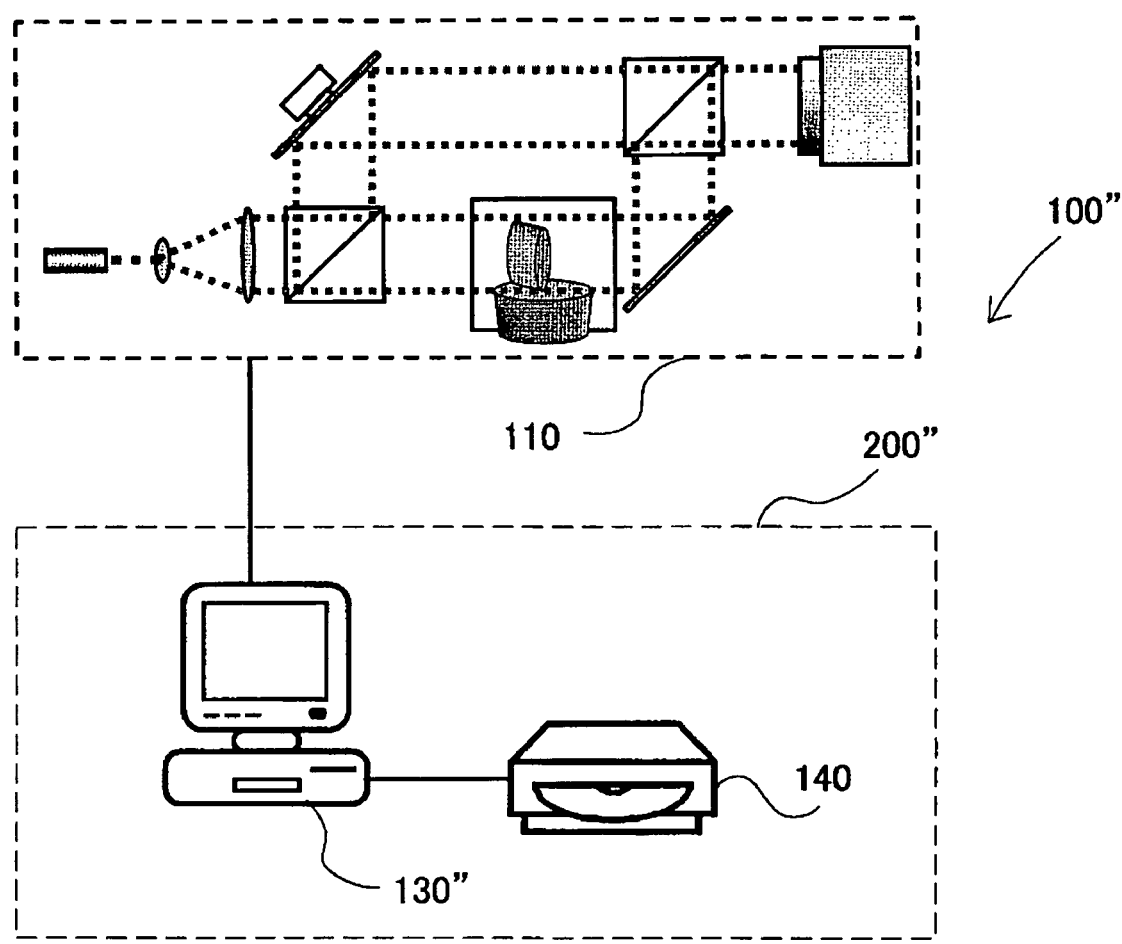
FIG. 7 shows the structure of a refractive index distribution measuring apparatus which is Embodiment 3 of the present invention.

FIG. 7 shows an example of the structure of a refractive index distribution measuring apparatus 100" which includes an image processing apparatus and an interferometer of Embodiment 3. The refractive index distribution measuring apparatus 100" is comprised of an interferometer 110 and an image processing apparatus 200". The image processing apparatus 200" is comprised of a refractive index distribution generator 130" and a refractive index distribution recorder 140. The refractive index distribution generator 130" is formed of a single personal computer. The respective components which constitute the interferometer 110 and the image processing apparatus 200" are formed such that they can communicate data with each other through a bus interface, for example.

The interferometer 110 and the refractive index distribution recorder 140 are similar to those in Embodiment 2, but the refractive index distribution generator 130" processes measured interference fringes provided by the interferometer 110 and produces a refractive index distribution (output refractive index distribution data) within an object O under test, a transmittance distribution, and a reference light phase. The refractive index distribution and transmittance distribution are three-dimensional volume data which shows how the refractive index and transmittance are distributed within the object O, in which the error is at the minimum between the measured interference fringes and estimated interference fringes which are presumably provided if the object O has such a refractive index distribution and a transmittance distribution and is measured in a similar manner to that with the interferometer 110. In addition, each of the distributions has a natural distribution. The method therefor will be described later in detail.

Next, description will hereinafter be made of the more detailed operation of each component of the refractive index distribution measuring apparatus 100". In interference fringe measurement, while the object O is set on a rotation mechanism 106 of the interferometer 110, the rotation mechanism 106 and a piezoelectric mirror 104 are driven to take (record) an image of interference fringes at a rotation position $R_i$ by an image-taking apparatus 109. At this point, it is not necessary to know the reference light phase, and the piezoelectric mirror 104 of the interferometer 110 can be randomly driven or fixed. When the piezoelectric mirror 104 is fixed, it may be replaced with a typical (fixed) mirror to provide a constant reference light phase. The taken image is output as measured interference fringes.

After the image-taking is completed, the rotation mechanism 106 and the piezoelectric mirror 104 are operated to set the object O to another rotation position $R_{i+1}$ to repeat the image-taking similarly. The number of rotation positions at which images are taken depends on the ultimately required resolution or accuracy in the refractive index distribution.

The measured interference fringes F thus taken can be expressed as $F(R_i, x, y)$ with each rotation position $R_i$, where x and y represent coordinates on the image. The measured interference fringes F taken as images are input to the refractive index distribution generator 130".

The refractive index distribution generator 130" estimates a three-dimensional refractive index distribution N (u, v, w) of the object O from the measured interference fringes $F(R_i, x, y)$ measured in the plurality of light ray directions and also estimates a transmittance distribution T(u, v, w) and a reference light phase $\theta_i$.

Figure 8:
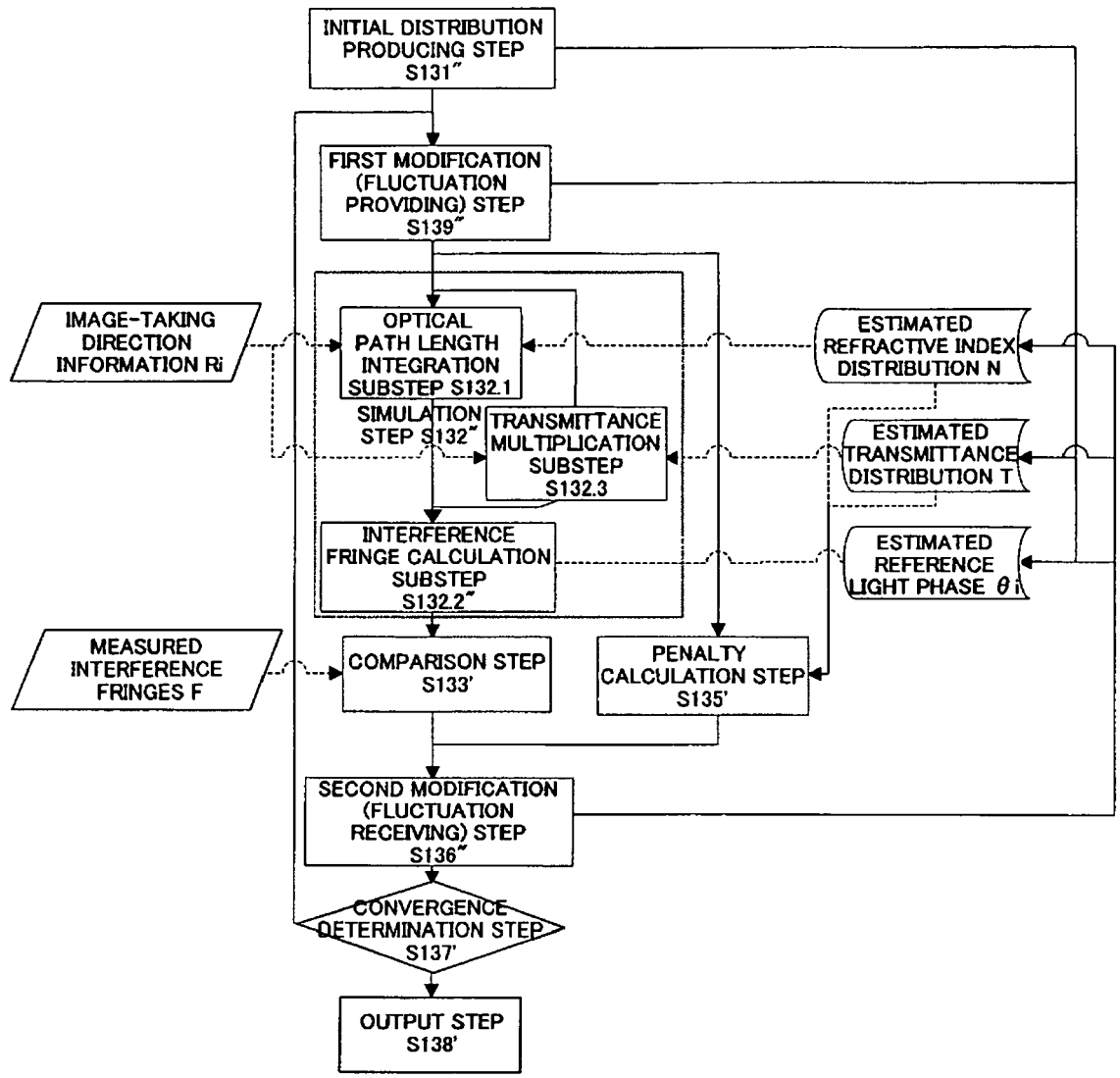
FIG. 8 is a flow chart showing the operation of a refractive index distribution generator which forms part of the refractive index distribution measuring apparatus of Embodiment 3.

The operation of the refractive index distribution generator 130" will be described with reference to a flow chart of FIG. 8. The processing of the refractive index distribution generator 130" is basically the same as that in Embodiment 2, and is comprised of an initial distribution producing step S131, a first modification (fluctuation providing) step S139", a simulation step S132", a comparison step S133', a penalty calculating step S135', a second modification (fluctuation receiving) step S136", a convergence determination step S137', and an output step S138. Of them, the first modification step S139" to the convergence determination step S137' form a repetitive loop which is repeated over a plurality of times.

The refractive index distribution generator 130" receives as input data the interference fringe image $F(R_i, x, y)$ and the information of the rotation position (image-taking direction) $R_i$ at the time of taking the respective interference fringes and holds as a variable an estimated refractive index distribution N(u, v, w) as well as an estimated refractive index distribution T(u, v, w) and an estimated reference light phase $\theta_i$.

First, at the initial distribution producing step S131", the refractive index distribution generator 130" produces an initial distribution $N^0$ of an estimated refractive index distribution $N^n$ and produces initial distributions $T^0$ and $\theta_i^0$ of the estimated transmittance distribution $T^n$ and the estimated reference light phase $\theta_i^n$, respectively.

At the first modification step S139", the refractive index distribution generator 130" provides a random change for the estimated refractive index distribution $N^n$, and also provides a random change for each of the estimated transmittance distribution $T^n$ and the estimated reference light phase $\theta_i^n$.

The simulation step S132" has an optical path length integration substep S132.1, an interference fringe calculation substep S132.2, and a transmittance multiplication substep S132.3 to simulate the process of producing the interference fringes in the interferometer 110 to produce estimated interference fringes $F^n$.

At the optical path length integration substep S132.1, the refractive index distribution generator 130" produces an estimated transmitted wavefront $I^n$ for the estimated refractive index distribution $N^n$, similarly to Embodiment 2.

At the transmittance multiplication substep S132.3, the refractive index distribution generator 130" produces an estimated transmitted light intensity image $J^n$ presumably provided if the estimated transmittance distribution $T^n$ is the transmittance distribution T of the object O. To this end, the following expression is used in consideration of the rotation position $R_i$ at the time of the interference fringe measurement:

$$J^n(R_i, x, y) = \exp\left[\int \log\{T^n(u(R_i, x, y, z), v(R_i, x, y, z), w(R_i, x, y, z)\}dz\right]$$

where $u(R_i, x, y, z)$, $v(R_i, x, y, z)$, and $w(R_i, x, y, z)$ are the same as those in the expressions (3a) and (3b).

At the interference fringe calculation substep S132.2", the refractive index distribution generator 130" produces the estimated interference fringes $F^n$ from the estimated transmitted wavefront $I^n$ produced at the optical path length integration substep S132.1 and the estimated transmitted light intensity image $J^n$ produced at the transmittance multiplication substep S132.3. To this end, the following expression is used in consideration of the estimated reference light phase $\theta_i^n$:

$$F^n\{Ri, x, y\} = \frac{F_0}{2}\sqrt{1 + 2J^n\cos(I^n - \theta_i^n) + J^{n2}} \quad (15)$$

where $F^0$ represents an image intensity provided by the image-taking apparatus 109 when the transmitted light has a transmittance of 100% and has the same phase as the reference light, and is the maximum value which the measured interference fringes $F(R_i, x, y)$ can take if noise is ignored.

At the comparison step S133', similarly to Embodiment 2, the refractive index distribution generator 130" compares the estimated interference fringes $F^n$ provided at the simulation step S132" with the measured interference fringes F actually provided by the interferometer 110 and inputs the difference $d^n(R_i, x, y) = F(R_i, x, y) - F^n(R_i, x, y)$ (first information) to the second modification step S136".

On the other hand, at the penalty calculation step S135", the refractive index distribution generator 130" calculates a penalty function P(N", T") defined for the estimated refractive index distribution N" and the estimated transmittance distribution T", and inputs it to the second modification step S136". The penalty function represents the "unnaturalness" of the estimated refractive index distribution N" and the estimated transmittance distribution T". For example, the refractive index distribution and the transmittance distribution are assumed to be continuous ones, and as the penalty, P(N", T") is defined as follows:

$$P(N'', T'') = (\nabla N'')^2 + k(\nabla T'')^2$$

which is the linear sum of the square norms of spatial variations $\nabla N''$ and $\nabla T''$ of N" and T", respectively. If it is known that the refractive index is positively correlated with the transparency, its influence may be considered and the following may be used:

$$P(N'', T'') = (\nabla N'')^2 + k_1(\nabla T'')^2 - k_2(\nabla N'' \nabla T'')$$

where k, $k_1$, and $k_2$ represent positive values for weighting in the respective terms.

At the second modification step S136", the refractive index distribution generator 130" modifies (changes) the estimated refractive index distribution N" based on the estimated error d" provided at the comparison step S133" and P(N", T") provided at the penalty calculation step S135". It also modifies the estimated transmittance distribution T" and the estimated reference light phase (first reference wavefront data) $\theta_i''$. To this end, it compares the following:

$$E^n = \left(\frac{d^n}{\sigma_F}\right)^2 + \beta P(N^n, T^n) \quad (16)$$

which is the current evaluation value (second information) with the following:

$$E^{n-1} = \left(\frac{d^{n-1}}{\sigma_F}\right)^2 + \beta P(N^{n-1}, T^{n-1}) \quad (17)$$

which is the previous evaluation value. If the increase amount $\Delta E = E^n - E^{n-1}$ is a positive value, the refractive index distribution generator 130" returns the estimated refractive index distribution N", the estimated transmittance distribution T", and the estimated reference wavefront $\theta_i''$ to the values $N^{n-1}$, $T^{n-1}$, and $\theta_i^{n-1}$, respectively, before the execution of the preceding first modification step 139" at the probability of $P = 1 - \exp(-\Delta E/T)$.

At the convergence determination step S137', similarly to Embodiment 2, the value of a control parameter T is referred to, and the flow proceeds to the output step S138 if the value of T is lower than a predetermined threshold, or to the first modification step S139" if not. At this point, the estimated refractive index distribution, the estimated transmittance distribution, and the estimated reference wavefront input to the first modification step S139" are the estimated refractive index distribution, estimated transmittance distribution, and estimated reference wavefront which are newly produced in the modification at the second modification step 136".

At the output step S138, the estimated refractive index distribution $N'''$ at that point is output as a final refractive index distribution of the refractive index distribution generator 130". When the reduction in the control parameter T is sufficiently slow, the final refractive index distribution N is provided at a high probability to minimize the value expressed by:

$$\left(\frac{d}{\sigma_F}\right)^2 + \beta P(N, T) \quad (18)$$

similarly to Embodiment 2. It should be noted that not only the final refractive index distribution N but also the estimated transmittance distribution $T'''$ and the estimated reference wave phase $\theta_i'''$ may be output as the transmittance distribution T and the reference wavefront $\theta_i$, respectively, as required.

In Embodiment 3, similarly to Embodiment 2, since the final refractive index distribution N output from the refractive index distribution generator 130" is a relative value of the phase change amount per unit length to the matching liquid, transformation thereof to a refractive index in a standard unit requires the following calculation:

$$N = \frac{\lambda}{2\pi}N + N_0 \quad (19)$$

where $\lambda$ represents the wavelength of the laser light, and $N_0$ represents the refractive index of the matching liquid.

The refractive index distribution recorder 140 records the final refractive index distribution N produced by the refractive index distribution generator 130". Not only the refractive index distribution N but also the estimated transmittance distribution T and the estimated reference wave phase $\theta_i$ may be recorded as required.

According to Embodiment 3, since the reference light phase and the transmittance distribution are estimated in addition to the refractive index distribution, they do not need to be determined in advance, and thus it is possible to use an object under test with an unknown transmittance distribution or an interferometer with an uncertain reference light phase due to influences of atmospheric fluctuations or the like.

In addition, if it is known that the reference wavefront is constant in all interference fringe measurements, for example when the piezoelectric mirror 104 is fixed and atmospheric fluctuations are negligible, the refractive index distribution can be determined with higher accuracy by using existing information, for example by setting the estimated reference wavefront $\theta_i$ to the same value $\theta$.

Embodiment 4

Figure 10:
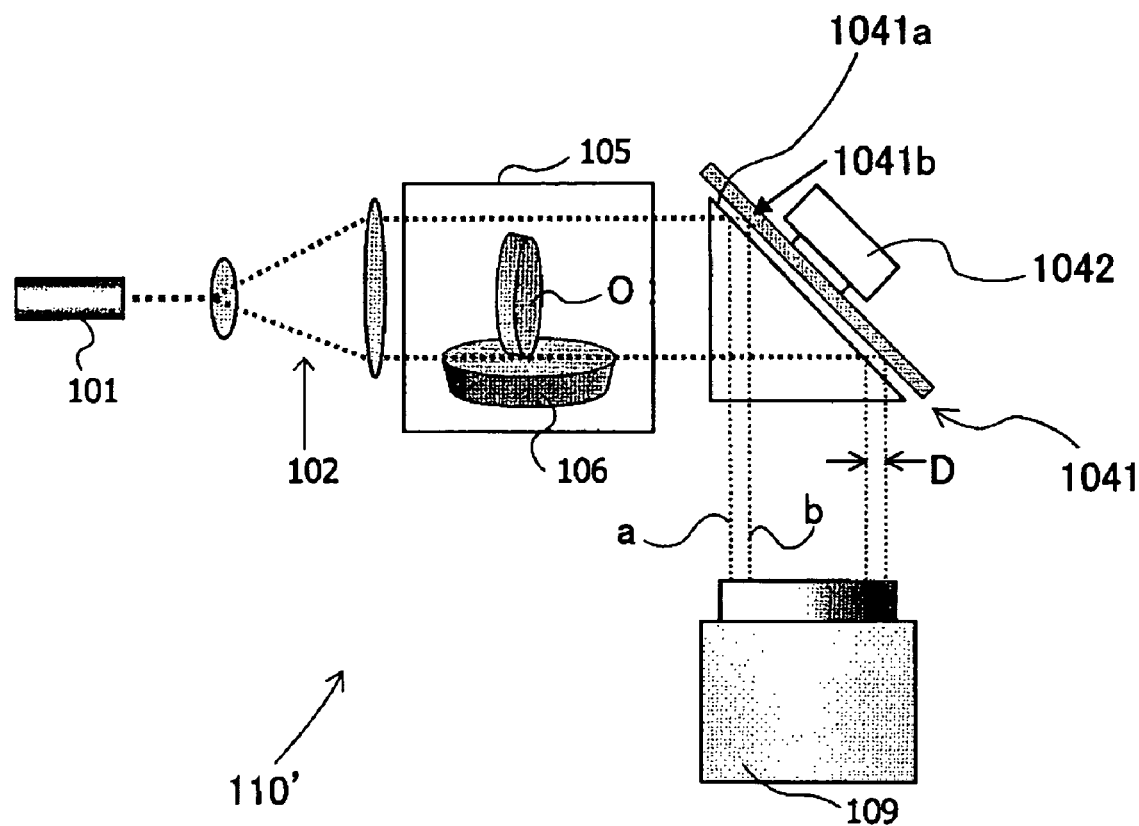
FIG. 10 shows the structure of a shearing interferometer used in the refractive index distribution measuring apparatus of Embodiment 4.

While Embodiment 2 has been described in conjunction with the use of the interference fringe image measured by the two-beam interferometer shown in FIG. 2, an interference fringe image measured by a shearing interferometer, for example as shown in FIG. 10, can be used to produce refractive index data within an object O under test. An image processing method for use in that case will hereinafter be described.

Figure 9:
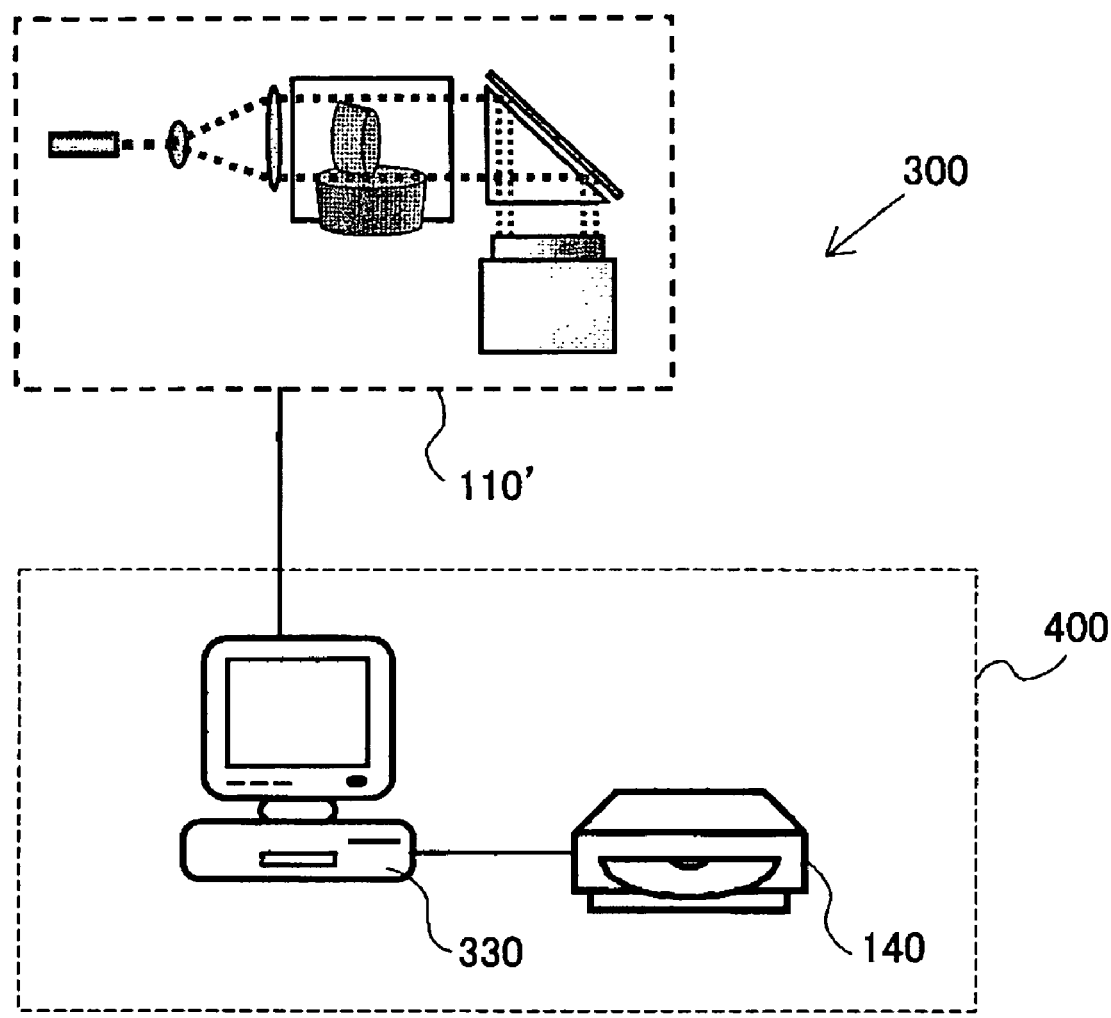
FIG. 9 shows the structure of a refractive index distribution measuring apparatus which is Embodiment 4 of the present invention.

FIG. 9 shows an example of the structure of a refractive index distribution measuring apparatus 300 which includes an image processing apparatus and an interferometer in Embodiment 4. The refractive index distribution measuring apparatus 300 is comprised of a shearing interferometer 110' and an image processing apparatus 400 which has a refractive index distribution generator 330 and a refractive index distribution recorder 140. The refractive index distribution generator 330 is formed of a single personal computer. The respective components which constitute the interferometer 110' and the image processing apparatus 400 are formed such that they can communicate data with each other through a bus interface, for example.

The shearing interferometer 110' is formed to allow observation of interference fringes of light transmitted through the object O in a plurality of different light ray directions. As shown in FIG. 10, the searing interferometer 110' is comprised of a laser light source 101, a beam expander 102, a shearing mirror 1041, a matching bath 105, a rotation mechanism 106, and an image-taking apparatus 109. Of the components, those other than the shearing mirror 1041 are identical to those of the interferometer 110 described in Embodiment 1.

The shearing mirror 1041 includes a semireflecting surface 1041a and a total reflecting surface 1041b disposed substantially in parallel with a predetermined interval between them. A luminous flux transmitted through the object O and incident on the shearing mirror 1041 is split into a luminous flux a reflected by the semireflecting surface 1041a and a luminous flux b reflected by the total reflecting surface 1041b, and they are superposed and emerge from the mirror 1041 with a gap between them. In Embodiment 4, the gap is set to a shearing width D and the direction (shearing direction) is set to a y-axis direction of an image. The total reflecting surface 1041b is formed to be translated back and forth (in the direction toward the semireflecting surface 1041a and the direction away from it) by a perturbation apparatus 1042, and the translation can change the shearing width D. The superposed light rays emerging from the shearing mirror 1041 interfere with each other, and the resulting interference fringes are taken by an image-taking apparatus 109. The taken image is output as a measured interference fringe image.

In Embodiment 4, similarly to Embodiments 1 to 3, in the interference fringe measurement, the object O is set on the rotation mechanism 106 in the matching bath 105, and the matching bath 105 is filled with a liquid (a matching liquid) with substantially the same refractive index as that of the object O. The rotation mechanism 106 is driven to change the orientation of the object O to take images of interference fringes in a plurality of light ray directions.

The refractive index distribution generator 330 processes the measured interference fringe image (hereinafter referred to simply as measured interference fringes) provided by the shearing interferometer 110' to produce refractive index distribution data (hereinafter referred to simply as a refractive index distribution) within the object O, similarly to the abovementioned refractive index distribution generator 130' of Embodiment 2. The method therefor will be described later in detail. The refractive index distribution recorder 140 is similar to that in Embodiment 2.

Next, description will hereinafter be made of the more detailed operation of each component of the refractive index distribution measuring apparatus 300. In interference fringe measurement, while the object O is set on the rotation mechanism 106 of the shearing interferometer 110', the rotation mechanism 106 and the perturbation apparatus 1042 are driven to take (record) an image of interference fringes at a rotating position $R_i$ and a shearing width $D_i$ by an image-taking apparatus 109.

After the image-taking is completed, the rotation mechanism 106 and the perturbation apparatus 1042 are operated to set the object O to another rotation position $R_{i+1}$ and another shearing width $D_{i+1}$ and image-taking is repeated similarly. The number of rotation positions at which images are taken depends on the ultimately required resolution or accuracy in the refractive index distribution.

Measured interference fringes F thus taken can be expressed as $F(R_i, D_i, x, y)$ with each rotation position $R_i$ and shearing width $D_i$, where x and y represent coordinates on the image. The measured interference fringes F taken as the images are input to the refractive index distribution generator 330.

For simplify the description, it is assumed that the luminous flux a and the luminous flux b in the shearing interferometer 110' have the equal intensity, and the intensity of the light superposed at the same phase is equal to one.

Figure 11:
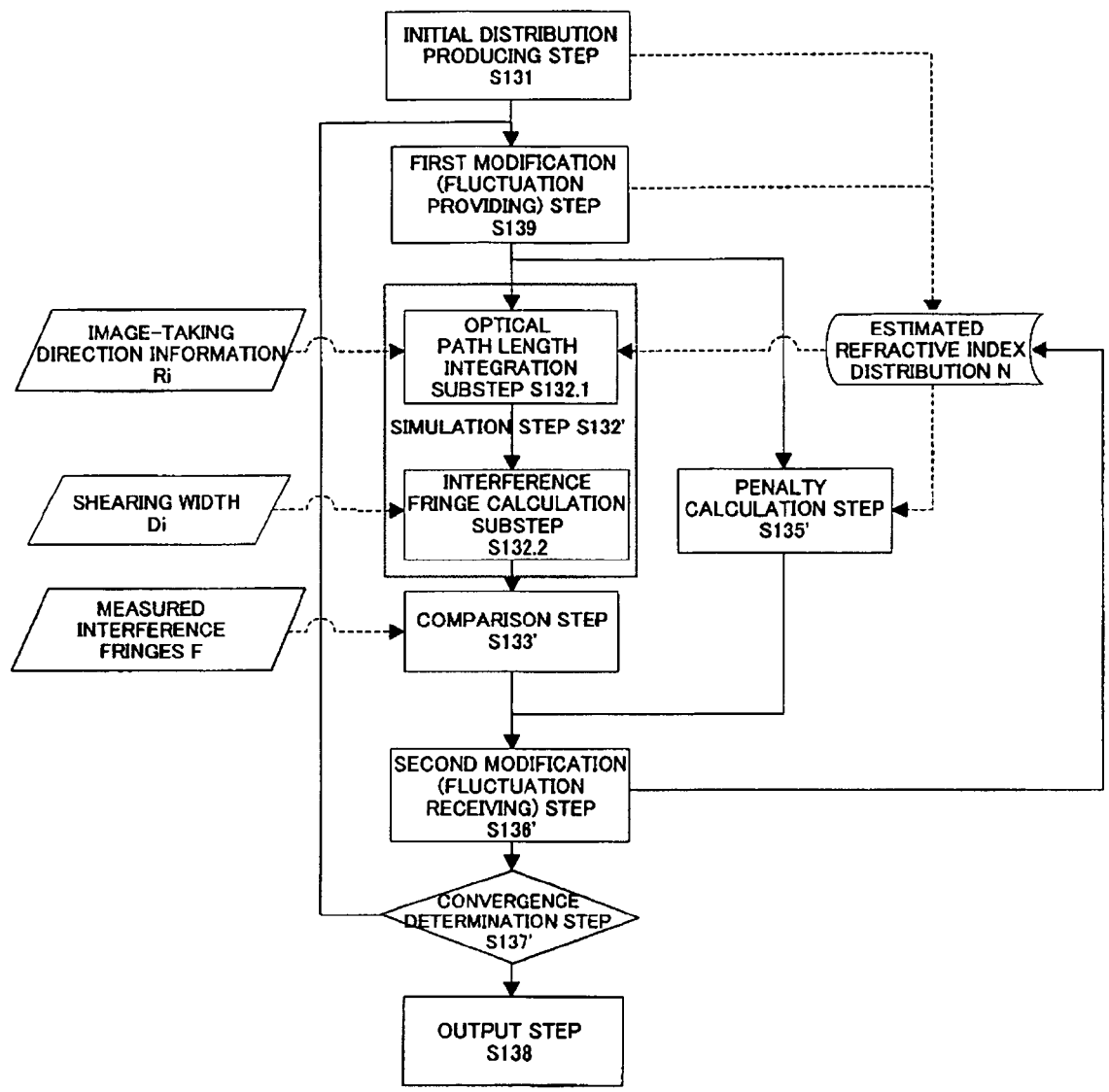
FIG. 11 is a flow chart showing the operation of a refractive index distribution generator which forms part of the refractive index distribution measuring apparatus of Embodiment 4.

The refractive index distribution generator 330 estimates a three-dimensional refractive index distribution N(u, v, w) of the object O from the interference fringe image $F(R_i, D_i, x, y)$ of the object O measured in the plurality of light ray directions by the shearing interferometer 110'. FIG. 11 shows a flow chart of the operation of the refractive index distribution generator 330.

The flow chart of FIG. 11 is substantially the same as that in Embodiment 2 (FIG. 6) except that the shearing width $D_i$ is input instead of the reference light phase information $\theta_i$ in Embodiment 2 as input data to an interference fringe calculation substep S132.2 of a simulation step S132'.

At an optical path length integration substep S132.1 in the simulation step S132', similarly to Embodiment 2, the refractive index distribution generator 330 integrates an estimated refractive index distribution N" at each light ray direction (rotation position) to calculate an estimated transmitted wavefront I" (transmitted wavefront image).

At the interference fringe calculation substep S132.2 in which the shearing width $D_i$ is referred to, the refractive index distribution generator 330 produces estimated interference fringes F" for the estimated transmitted wavefront $I''(R_i, D_i, x, y)$ produced at the interference fringe calculation substep S132.1 as follows:

$$F''(R_i, D_i, x, y) = \sqrt{\frac{1 + \cos(I''(R_i, D_i, x, y) - I''(R_i, D_i, x, y - D_i))}{2}} \quad (20)$$

where $I''(R_i, D_i, x, y-D_i)$ means the shearing image of the estimated transmitted wavefront I". In other words, the estimated interference fringes F" are produced by combining the estimated transmitted wavefront I" with the shearing image.

The remaining steps are performed similarly to those in Embodiment 2 to determine the optimal N as a refractive index distribution within the object O.

In this manner, in Embodiment 4, the shearing interferometer can be used as the interferometer to realize a compact apparatus as compared with those in Embodiments 1 to 3. Also, an object under test with a significantly nonuniform refractive index distribution can be used. In Embodiment 4, the rotation axis of the object O can be arranged not in parallel with the shearing direction, which can reduce periodic noise which tends to occur in the shearing interferometer.

It should be noted that the shearing width D does not necessarily have a variable value, and all the shearing width $D_i$ may be set to be the same value. In this case, the perturbation apparatus 1042 is not required.

Figure 12:
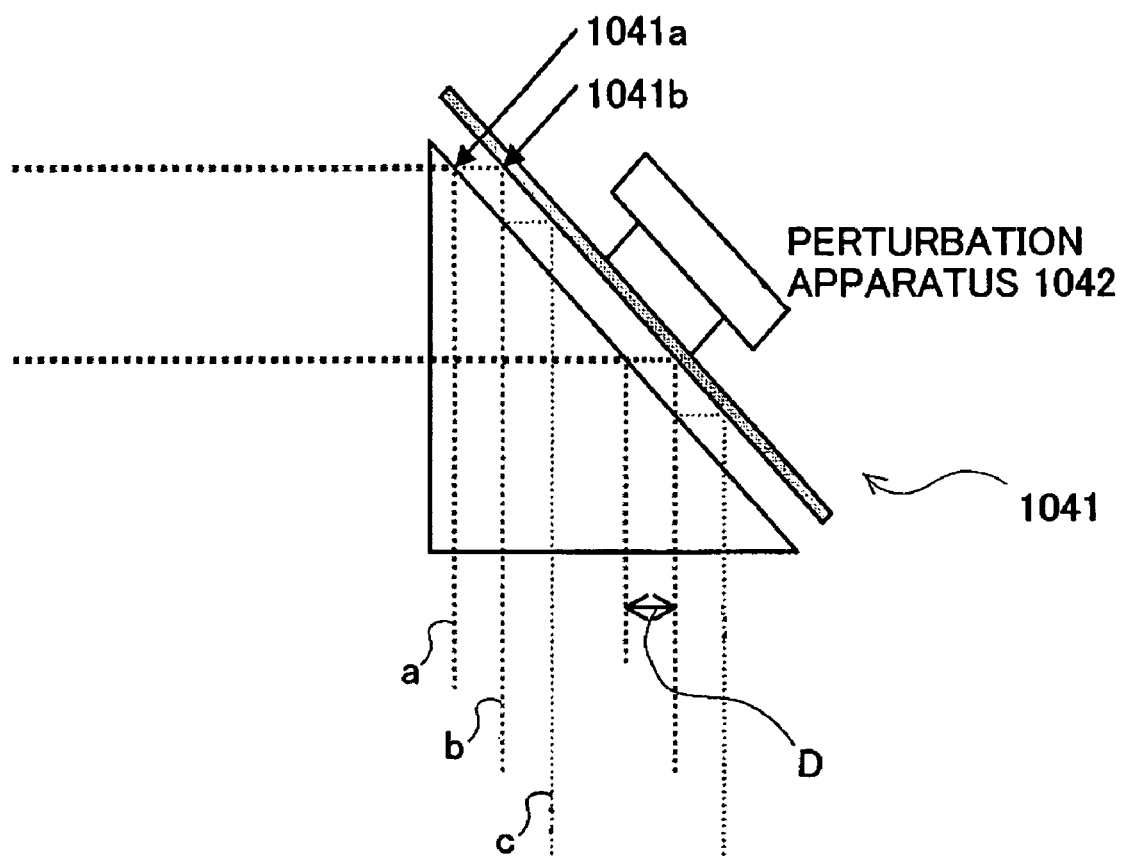
FIG. 12 is a schematic diagram for explaining occurrence of ghost light in the shearing interferometer.

In the expression (20), the luminous fluxes a and b reflected by the semireflecting surface and the total reflecting surface, respectively, have the same intensity and their sum is normalized to one. Strictly speaking, however, as shown in FIG. 12, the luminous flux b reflected by the total reflecting surface 1141b is further reflected by the back side of the semireflecting surface 1041a and again reflected by the total reflecting surface 11041b to cause a ghost luminous flux c toward the image-taking apparatus 109. In view of that, when the luminous fluxes a, b, and c have intensities expressed as a:b:c, the following may be used instead of the expression (20) to produce the estimated interference fringe image $F^n$:

$$F^n(R_i, D_i, x, y) = |a \exp\{jI^n(R_i, D_i, x, y)\} +$$
$$b \exp\{jI^n(R_i, D_i, x, y - D_i)\} + c \exp\{jI^n(R_i, D_i, x, y - 2D_i)\}|$$

where j represents an imaginary unit.

In this manner, the simulation step S132' can be used to model the interferometer used in taking the interference fringe image to support interferometers of various types.

Embodiment 5

As processing different from the processing in the refractive index distribution generator 330 in Embodiment 4 described above, the three-dimensional refractive index distribution N(u, v, w) of the object O can be expressed as a coefficient sequence $\{A_k\}=\{A_1, A_2, A_3, \ldots, A_k\}$ in the following:

$$N(u, v, w) = \sum_{k=1}^{K} A_k f_k(u, v, w) \quad (21)$$

as an approximate function with a predetermined term sequence $\{f_k(u, v, w)\}=\{f_1(u, v, w), f_2(u, v, w), f_3(u, v, w) \ldots, f_k(u, v, w)\}$. In other words, the coefficient sequence can be handled as refractive index distribution data.

As an example, when the term sequence is the following fourth-order three-dimensional Fourier term sequence expressed by:

$$\{\exp(2\pi j(W_u u + W_v v + W_w w))\}$$

where $-4 \leq W_u \leq 4$, $-4 \leq W_v \leq 4$, and $-4 \leq W_w \leq 4$, then the number of terms K is equal to $9^3$, that is, 279.

Figure 13:
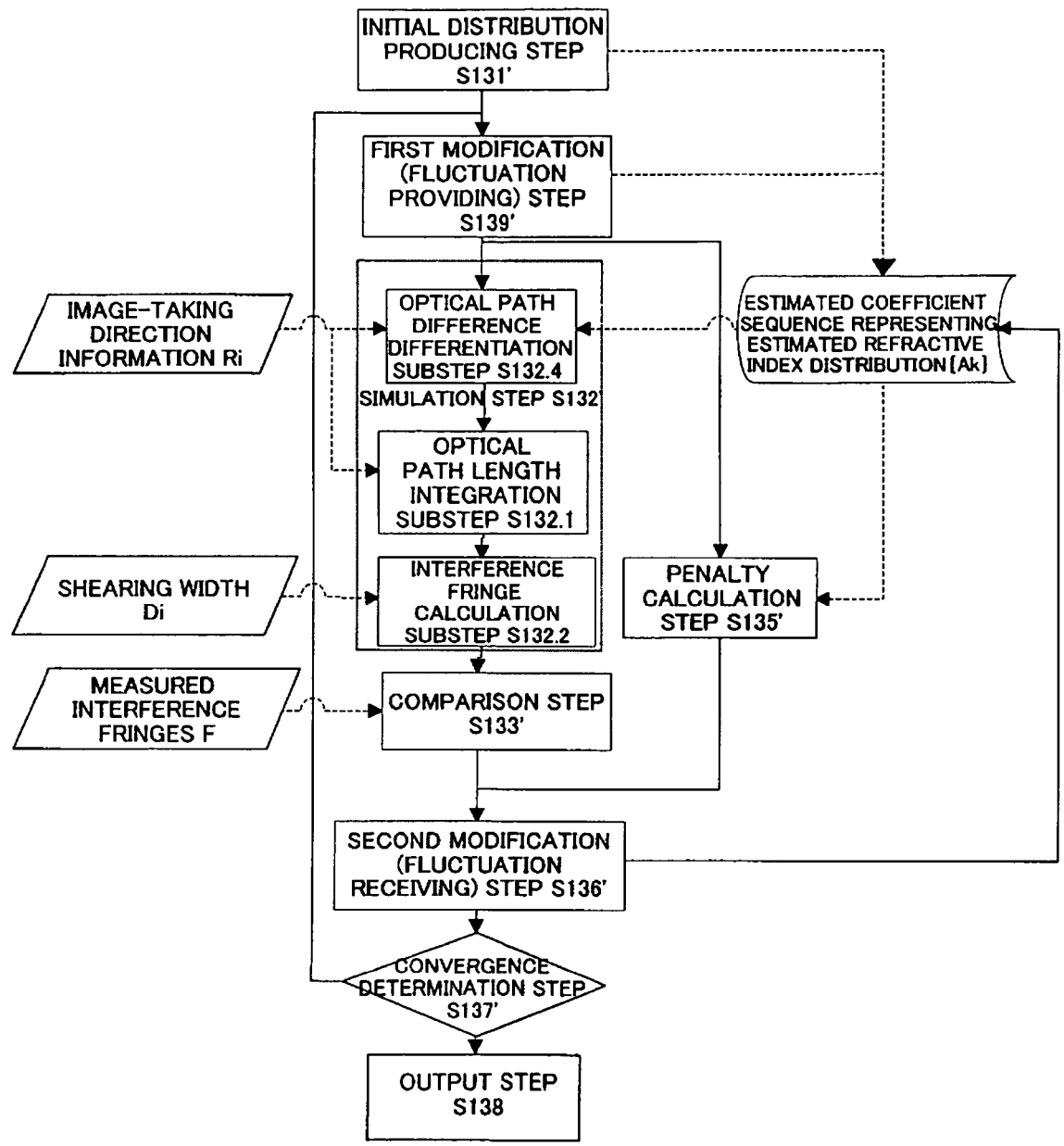
FIG. 13 is a flow chart showing the operation of a refractive index distribution generator which forms part of a refractive index distribution measuring apparatus of Embodiment 5.

The operation of a refractive index distribution generator 330 will be described with reference to a flow chart of FIG. 13. The processing of the refractive index distribution generator 330 is comprised of an initial distribution producing step S131, a first modification (fluctuation providing) step S139, a simulation (optical path length integration) step S132', a comparison step S133', a penalty calculating step S135', a second modification (fluctuation accepting) step S136', a convergence determination step S137', and an output step S138. Of them, the first modification (fluctuation providing) S139' to the convergence determination step S137' form a repetitive loop which is repeated over a plurality of times.

The refractive index distribution generator 330 receives as input data measured interference fringes $F(R_i, D_i, x, y)$ and the information of a shearing width $D_i$ at the time of taking each transmitted wavefront and holds as a variable an estimated coefficient sequence $\{A_k\}$ indicating an estimated refractive index distribution N.

First, at the initial distribution producing step S131', the refractive index distribution generator 330 produces an initial estimated coefficient sequence $\{A_k\}^0$ of an estimated coefficient sequence $\{A_k\}^n$. Since the initial estimated coefficient sequence $\{A_k\}^0$ produced at this step does not affect the finally produced coefficient sequence, any coefficient sequence may be used, and for example, a null sequence $\{A_k\}^0=0$ is used.

At the first modification (fluctuation providing) step S139', the refractive index distribution generator 330 provides a random change for the estimated coefficient sequence $\{A_k\}^n$.

The simulation step S132' is comprised of an optical path difference differentiation substep S132.4, an optical path length integration substep S132.1', and an interference fringe calculation substep S132.2'. At the optical path difference differentiation substep 132.4, the refractive index distribution generator 330 determines an estimated refractive index difference per unit shearing width at each rotation position $R_i$ expressed by:

$$\frac{d}{dy} N_i^n(u, v, w) \quad (22)$$

with the following expression:

$$\frac{d}{dy} N_i^n(u, v, w) = \quad (23)$$
$$\sum_{k=1}^{K} A_k^n \left( \frac{d f_k(u, v, w)}{du} \frac{du(R_i.x.y.z)}{dy} + \frac{d f_k(u, v, w)}{dv} \frac{dv(R_i.x.y.z)}{dy} + \frac{d f_k(u, v, w)}{dw} \frac{dw(R_i.x.y.z)}{dy} \right)$$

where $u(R_i, x, y, z)$, $v(R_i, x, y, z)$, and $w(R_i, x, y, z)$ are identical to those in the expressions (3a) and (3b). The following:

$$\frac{du(R_i.x.y.z)}{dy}, \frac{dv(R_i.x.y.z)}{dy}, \frac{dw(R_i, x, y, z)}{dy} \quad (24)$$

is the second column of a rotating matrix $Rot(R_i)^{-1}$.

At the next optical path length integration substep S132.1', the refractive index distribution generator 330 integrates the estimated refractive index difference expressed by:

$$\frac{d}{dy} N_i^n(u, v, w) \quad (25)$$

in the light ray direction and determines an estimated transmitted wavefront difference $I^n(R_i, x, y)$ per unit shearing width as follows:

$$\frac{d}{dy}I^n(R_i, x, y) = \tag{26}$$

$$\int \frac{d}{dy} N_i^n \{u(R_i, x, y, z), v(R_i, x, y, z), w(R_i, x, y, z)\} dz$$

In addition, at the interference fringe calculation substep S132.2', estimated interference fringes F" are produced as follows:

$$F^n(R_i, D_i, x, y) = \sqrt{\frac{1 + \cos\left(D_i \frac{d}{dy} I^n(R_i, x, y)\right)}{2}} \tag{27}$$

At the comparison step S133', similarly to Embodiment 2, the refractive index distribution generator 330 compares the estimated interference fringes F" provided at the simulation step S132' with the measured interference fringes F actually provided by the shearing interferometer 110' and inputs the difference $d''(R_i, x, y) = F(R_i, x, y) - F''(R_i, x, y)$ to the second modification step S136' as an estimated error (first information).

On the other hand, at the penalty calculation step S135', the refractive index distribution generator 330 calculates a penalty function $P(\{A_k\}^n)$ defined for the estimated coefficient sequence $\{A_k\}^n$. For example, when it is assumed that a refractive index distribution N" represented by $A_k^n$ is a smooth distribution with a small amount of high-frequency components, the wave number of the term $f_k$ associated with $A_k^n$ expressed by:

$$W_k = \sqrt{W_{uk}^2 + W_{vk}^2 + W_{wk}^2} \tag{28}$$

is used to calculate as $P(\{A_k\}^n) = \Sigma_k |A_k^n| W_K$.

At the second modification step S136', the refractive index distribution generator 330 modifies (changes) the estimated coefficient sequence $\{A_k\}$ based on the estimated error d" provided at the comparison step S133' and the penalty function $P(\{A_k\}^n)$ provided at the penalty calculation step S135'. To this end, the refractive index distribution generator 330 compares the following:

$$E^n = \left(\frac{d^n}{\sigma_F}\right)^2 + \beta P(\{A_k\}^n) \tag{29}$$

which is the current evaluation value (second information) with the following:

$$E^{n-1} = \left(\frac{d^{n-1}}{\sigma_F}\right)^2 + \beta P(\{A_k\}^n) \tag{30}$$

which is the previous evaluation value, and if the increase amount $\Delta E = E^n - E^{n-1}$ is a positive value, it returns the estimated coefficient sequence $\{A_k\}^n$ to the value $\{A_k\}^{n-1}$ before the execution of the preceding first modification step 139' at the probability of $P = 1 - \exp(-\Delta E/T)$. T represents a control parameter having a positive value and is appropriately reduced as the process is repeated.

At the convergence determination step S137', similarly to Embodiment 2, the refractive index distribution generator 330 refers to the value of the control parameter T, and the flow proceeds to the output step S138 if the value of T is lower than a predetermined threshold, or to the first modification step S139' if not.

At the output step S138, the estimated refractive index distribution $\{A_k\}^n$ at that point is output as a final refractive index distribution (output refractive index distribution data) N of the refractive index distribution generator 330.

In Embodiment 5, similarly to Embodiment 2, since $\{A_k\}$ output from the refractive index distribution generator 330 is a relative value of the phase change amount per unit length to the matching liquid, transformation thereof to a refractive index in a standard unit requires the following calculation:

$$A_k = \frac{\lambda}{2\pi} A_k + N_0 \quad \text{(CONSTANT TERM)} \tag{31}$$

$$A_k = \frac{\lambda}{2\pi} A_k \quad \text{(OTHER TERM)}$$

where $\lambda$ represents the wavelength of the laser light, and $N_0$ represents the refractive index of the matching liquid.

The refractive index distribution N represented by the coefficient sequence $\{A_k\}$ thus provided:

$$N(u, v, w) = \sum_{k=1}^{K} A_k f_k(u, v, w) \tag{32}$$

is optimal as the refractive index distribution within the object O.

When the refractive index distribution is used for optical design or the like, representation in expressions is often more desirable than representation in voxels, and the present invention is preferable in that case. When an appropriate term sequence is given, the required number of coefficients to be determined is small than the number of voxels used in the voxel representation, so that the calculation amount necessary for the processing can be reduced.

The method which utilizes the estimated coefficient sequence representing the estimated refractive index distribution as in Embodiment 5 can be applied in the method described in Embodiment 1.

A supplemental description of the penalty in each of Embodiments 1 to 5 will be added. First, in Embodiment 1, the modification amount calculated at the modification step can be set to zero for the estimated refractive index distribution (the first refractive index distribution data) in which the penalty takes the extreme value, and the modification amount can be the gradient of the penalty. In addition, the modification amount can be set to a value to increase the penalty by adding it to the estimated refractive index distribution.

As described in Embodiment 1, the penalty can be represented as the sum of partial penalties which can be calculated for each part of the estimated refractive index distribution (the first refractive index distribution data), and the partial penalty can depend only on the refractive index in and near that part.

The penalty can be set to have a higher value as the estimated refractive index distribution represents a more nonuniform refractive index distribution. The penalty can includes a term positively correlated with the difference between the estimated refractive index distribution and the smoothed distribution. In addition, the penalty can be positively correlated with the amount of the high-frequency components in the estimated refractive index distribution.

As described above, according to each of Embodiments 1 to 5, the data indicating the internal refractive index distribution with high accuracy can be produced from the transmitted wavefront image or the interference fringe image measured by applying the light to the object in the plurality of directions (the light ray directions). In addition, since the plurality of directions are not limited to the direction orthogonal to a single rotation axis, transmitted wavefronts or interference fringes can be measured in various light ray directions to provide the internal refractive index distribution data with higher accuracy or higher resolution. The type of the interferometer is not limited, and for example, the shearing interferometer can be used to measure the internal refractive index distribution of an object with a significantly nonuniform internal refractive index distribution. Moreover, according to the latter present invention, highly accurate internal refractive index distribution data can be produced from the interference fringe image without changing the interference fringe image to the transmitted wavefront image. In other words, the refractive index distribution can be directly provided without recovering the transmitted wavefront from the interference fringes, so that errors from the phase recovery can be avoided.

This application claims a benefit of priority based on Japanese Patent Application No. 2005-012174, filed on Jan. 19, 2005, which is hereby incorporated by reference herein in its entirety as if fully set forth herein.

What is claimed is:

1. An image processing apparatus which uses a first transmitted wavefront image measured by applying light to an object in each of a plurality of directions to produce output refractive index distribution data showing a refractive index distribution within the object, the apparatus comprising:
   a simulating section which simulates a transmitted wavefront in each of the directions to produce a second transmitted wavefront image based on first refractive index distribution data;
   a comparing section which compares the second transmitted wavefront image with the first transmitted wavefront image to produce first information indicating the comparison result; and
   a changing section which changes the first refractive index distribution data based on the first information to produce second refractive index distribution data,
   wherein the image processing apparatus repeats each of the sections using the second refractive index distribution data as the first refractive index distribution data and produces the resulting second refractive index distribution data as the output refractive index distribution data.

2. The image processing apparatus according to claim 1, wherein the simulating section integrates the first refractive index distribution data in each of the directions to produce the second transmitted wavefront image.

3. The image processing apparatus according to claim 1, further comprising:
   a penalty calculating section which produces second information for use in changing the first refractive index distribution data based on a penalty function of the first refractive index distribution data,
   wherein the changing section changes the first refractive index distribution data based on the first information and the second information to produce the second refractive index distribution data.

4. The image processing apparatus according to claim 3, wherein the second information is a magnitude of the change of the first refractive index distribution data and is a value to increase the penalty by adding the second information to the first refractive index distribution data.

5. The image processing apparatus according to claim 4, wherein the penalty has a higher value as the first refractive index distribution data represents less homogeneous in the refractive index distribution.

6. An image processing apparatus which uses a first interference fringe image measured by an interferometer applying light to an object in each of a plurality of directions to produce output refractive index distribution data showing a refractive index distribution within the object, the apparatus comprising:
   a simulating section which simulates the process of producing interference fringes by the interferometer to produce a second interference fringe image based on first refractive index distribution data;
   a comparing section which compares the second interference fringe image with the first interference fringe image to produce first information indicating the comparison result; and
   a changing section which changes the first refractive index distribution data based on the first information to produce second refractive index distribution data,
   wherein the image processing apparatus repeats each of the sections using the second refractive index distribution data as the first refractive index distribution data and produces the resulting second refractive index distribution data as the output refractive index distribution data.

7. The image processing apparatus according to claim 6, wherein the interferometer uses transmitted light which is transmitted through the object and reference light which is not transmitted through the object to produce the first interference fringe image, and
   the simulating section produces the second interference fringe image based on the first refractive index distribution data and first reference wavefront data indicating a wavefront of the reference light.

8. The image processing apparatus according to claim 7, wherein the changing section produces the second refractive index distribution data and produces second reference wavefront data by changing the first reference wavefront data, and
   the simulating section uses the second reference wavefront data as the first reference wavefront data.

9. The image processing apparatus according to claim 7, wherein the simulating section integrates the first refractive index distribution data in each of the directions to produce a transmitted wavefront image indicating a wavefront of the transmitted light and produces the second interference fringe image based on the transmitted wavefront image and the first reference wavefront data.

10. The image processing apparatus according to claim 6, wherein the interferometer is a shearing interferometer, and
    the simulating section integrates the first refractive index distribution data in each of the directions to produce a transmitted wavefront image indicating a wavefront of the light transmitted through the object and produces the second interference fringe image based on the transmitted wavefront image and a shearing image thereof.

11. The image processing apparatus according to claim 6, further comprising:

a penalty calculating section which produces second information for use in changing the first refractive index distribution data based on a penalty function of the first refractive index distribution data, wherein the changing section changes the first refractive index distribution data based on the first information and the second information to produce the second refractive index distribution data.

12. The image processing apparatus according to claim 11, wherein the second information is a magnitude of the change of the first refractive index distribution data and is a value to increase the penalty by adding the second information to the first refractive index distribution data.

13. The image processing apparatus according to claim 12, wherein the penalty has a higher value as the first refractive index distribution data represents less homogeneous in the refractive index distribution.

14. A refractive index distribution measuring apparatus comprising:

the image processing apparatus according to claim 1; and
an interferometer which takes the first transmitted wavefront image.

15. A refractive index distribution measuring apparatus comprising:

the image processing apparatus according to claim 6; and
an interferometer which takes the first transmitted wavefront image.

16. A computer readable medium containing an image processing program which is executed on a computer and uses a first transmitted wavefront image measured by applying light to an object in each of a plurality of directions to produce output refractive index distribution data showing a refractive index distribution within the object, the program comprising:

a simulating step which simulates a transmitted wavefront in each of the directions to produce a second transmitted wavefront image based on first refractive index distribution data;

a comparing step which compares the second transmitted wavefront image with the first transmitted wavefront image to produce first information indicating the comparison result; and a changing step which changes the first refractive index distribution data based on the first information to produce second refractive index distribution data, wherein the image processing program repeats each of the steps using the second refractive index distribution data as the first refractive index distribution data and produces the resulting second refractive index distribution data as the output refractive index distribution data.

17. A computer readable medium containing an image processing program which is executed on a computer and uses a first interference fringe image measured by an interferometer applying light to an object in each of a plurality of directions to produce output refractive index distribution data showing a refractive index distribution within the object, the program comprising:

a simulating step which simulates the process of producing interference fringes by the interferometer to produce a second interference fringe image based on first refractive index distribution data;

a comparing step which compares the second interference fringe image with the first interference fringe image to produce first information indicating the comparison result; and a changing step which changes the first refractive index distribution data based on the first information to produce second refractive index distribution data, wherein the image processing program repeats each of the steps using the second refractive index distribution data as the first refractive index distribution data and produces the resulting second refractive index distribution data as the output refractive index distribution data.

* * * * *